United States Patent [19]
Wright et al.

[11] Patent Number: 5,795,368
[45] Date of Patent: Aug. 18, 1998

[54] MICROTRAP SAMPLE CONCENTRATOR AND METHODS OF USE

[75] Inventors: Lowell Wright, College Station; Scott M. Abeel, Bryan; Nathan C. Rawls; Ronald D. Snelling, both of College Station, all of Tex.

[73] Assignee: O.I. Corporation, College Station, Tex.

[21] Appl. No.: 609,447

[22] Filed: Mar. 1, 1996

[51] Int. Cl.$^6$ .......................... B01D 15/08; B01D 53/04
[52] U.S. Cl. .................. 95/82; 95/87; 95/89; 95/114; 95/126; 95/143; 96/105; 96/144; 96/146
[58] Field of Search ..................... 95/82, 87–90, 95/114–117, 126, 141, 143; 96/101, 105–108, 143–146

[56] References Cited

U.S. PATENT DOCUMENTS

| | | | |
|---|---|---|---|
| 4,003,257 | 1/1977 | Fletcher et al. | 95/87 X |
| 4,805,441 | 2/1989 | Sides et al. | 95/87 X |
| 5,250,093 | 10/1993 | Jiang et al. | |
| 5,358,557 | 10/1994 | Jiang et al. | |
| 5,402,668 | 4/1995 | Murakami et al. | 95/87 X |
| 5,447,556 | 9/1995 | Pleil et al. | 96/102 X |
| 5,470,380 | 11/1995 | Jiang et al. | |
| 5,547,497 | 8/1996 | Klemp et al. | 95/82 X |

OTHER PUBLICATIONS

*Don't Water Down Your Analysis! Get A+ in Purge & Trap Performance: Tekmark® 2000Plus with the New Moisture Control Module*, Tekmar Company, Cincinnati, Ohio (1991).

Tekmar, *OPTIC Injector Price List*, pp. 1–2, Unknown 91994).

Tekmar Company, *An OPTICal View of Programmed Temperature Vaporization*; Cincinnati, Ohio (Unknown).

Tekmar Company, *Specifications and Pricing, OPTIC and OPTIC 600 Specification*; Cincinnati, Ohio (Unknown).

Unknown, *Applications and Technical Notes*; (Unknown).

Janssen, H.G. et al., Chromatography Technical Notes No. 1, *Large volume sqmple introduction in Capillary Gas Chromatography*; Ai Cambridge Ltd. Seminar, pp. 1–2 (1993).

Janssen, H.G., Chromatography Technical Notes No. 2, *Selecting the Injection Mode in Capillary Chromatography*; Ai Cambridge Ltd. Seminar, pp. 1–4 (1993).

Wyllie, S.G., et al., Chromatography Technical Notes No. 3, *Use of a temperature programmable injector in the static and dynamic headspace analysis of aroma volatiles*; Riva del Garda Symposium, Italy, pp. 1–4 (1993).

Janssen, H.G., et al., Chromatography Technical Notes No. 5, *Analysing low volatility samples using high temperature PTV injection*; Ai Cambridge Ltd. Seminar, pp. 1–6 (1993).

Staniewski, J. et al., *Solvent Elimination Rate in Programmed Temperature Injections of Large Sample Volumes In Capillary GC*; 12th Int'l. Symposium on Capillary Chromatography, Japan, pp. 1–17 (1990).

(List continued on next page.)

*Primary Examiner*—Robert Spitzer
*Attorney, Agent, or Firm*—Fish & Richardson P.C.

[57] ABSTRACT

A microtrap sample concentrator useful for concentrating a sample of purged gas containing analytes for delivery to an analytical instrument, including: a tube containing at least one sorbent material which retains or traps analytes; where greater than 30% of all trapped analytes are directly delivered to an analytical instrument at a desorption flow rate of one to three cc/min, without splitting or cryogenic focusing the trapped analytes; where delivery of the trapped analytes to the analytical instrument is achieved by passing the trapped analytes through a passage being selectively connectable between the microtrap and the analytical instrument, the passage connected to a vent; where the temperature of the passage is not lower than ambient room temperature; and where the passage is heated to a temperature sufficient to vaporize water in the passage and to expel the vaporized water out of the vent.

65 Claims, 19 Drawing Sheets

OTHER PUBLICATIONS

Ridgeon, P.J., *A Universal Sample Introduction System for Capillary Columns*; Ai Cambridge Ltd. (Unknown).

Staniewski, J. et al., *Applicability of a Programmed Temperature Injector for Large Volume Sample Introduction in Capillary GC and for LC–GC Interfacing*; Fourteenth Int'l. Symposium on Capillary Chromatography. Baltimore, Maryland, pp. 654–662 (1992).

Hinshaw, J.V., GC Troubleshooting, Programmed–Temperature Inlets; IC–GC Int'l., vol. 5, No. 12, pp. 14–16 (Unknown).

Perkins, R., *The Use of PTV injection to enhance analytical Performance*; Tekmar Program of Seminars, Pittcon. (1994).

Tekmar Brochure, *2000 Series Concentrator Systems . . . for Volatile Organics Analysis by Purge and Trap or Dynamic Headspace*; Cincinnati, Ohio (Unknown).

Tekmar Brochure, *3000 Purge and Trap Concentrator*, Tekmar Company, Cincinnati, Ohio, pp. 1–16 (Unknown).

Chemical Data Systems, *CDS 380 Automated Purge and Trap System*; Oxford, PA (1988).

Chemical Data Systems, *CDS 330 GC Sample Concentrator, Programmed Cryo–Focusing Optimized for Direct Capillary GC*; Oxford, PA (1985).

Chemical Data Systems, *Model 330 Trapping Concentrator*, Oxford, PA (1988).

Chemical Data Systems, *Model 350/380 Autosampler*, Oxford, PA (1988).

O.I. Analytical, *Efficiency of Cryo–Focusing Traps for Puge–And–Trap Gas Chromatography*, Application Note 04040195; New Orleans, LA (1992).

O.I. Analytical, *GC/MS Analysis of Volatiles in Less Then 15 Minutes!*, Application Note 05250295; ChromConnection Newsletter (Jun., 1993).

O.I. Analytical Applications News 1992, Newsworthy, No. 0430493, *Use of a Cryo–Focusing Module™ as a Water Managemnt Tool in Purge–And–Trap/GC/MS Analysis*; New Orleans, La., pp. 1–25 (1992).

Allen K. Vickers, *An Automated Purge–and–Trap System for Analyzing Volatile Organic Compounds in Drinking Water*; O.I. Analytical Applications News 1991, Newsworthy, No. 02211091 (1991).

Alltech Environmental Update, *Volatile Organics Analysis: Building a State–of–the–Art Purge and Trap GC/MS System*; O.I. Analytical Applications News 1991, Newsworthy, No. 02970691 (1991).

Ho, J.S., et al., *A Fully Automated Purge–and–Trap System for Analyzing Volatile Organics in Drinking Water*, O.I. Analytical Applications News 1991, Newsworthy, No. 03330493 (1991).

O.I. Analytical Applications News 1991, Newsworthy, No. 03750991, *The Compatibility of the OI Analytical Purge and Trap with the HP 5971A MSD* (1991).

J&W Scientific, GC Environmental Applications Note #E3, *EPA 524.2 (Revision 4) With Extraordinary Speed and Resolution, 0 to 84 in 27.21 !* (1994).

*Tekmar® Model 1000 Capillary Interface*; Tekmar Company, Cincinnati, Ohio (Unknown).

Tekmar, *What is OPTIC?, Advantages of OPTIC*; Tekmar Company, Cincinnati, Ohio (Unknown).

Tekmar, *Primary Users, Applications*; Tekmar Company, Cincinnati, Ohio (Unknown).

Tekmar 3 x 5 card, *"Can You Make The Grade?", Purge and Trap Report Card*; Tekmar Company, Cincinnati, Ohio (Unknown).

Westendorf, R.G., *Design and performance of a microprocessor–based purge and trap concentrator*; American Laboratory, pp. 66–73 (1987).

Westendorf, R., *Managing Water in Purge & Trap GC/MS*; Environmental lab, pp. 36–39 (Aug./Sep. 1992).

Applications News 1992, Newsworthy, No. 0420493, *OI Analytical Model 4560 Sample Concentrator—Cyclone Water Management™ System*; O.I. Analytical, College Station, Texas (1992).

*Don't Water Down Your Analysis!, Tekmar 2000 Plus Purge and Trap™ Concentrator with Moisture Control Module*; Tekmar Company, Cincinnati, Ohio (Unknown).

Twachtman, J., *Form Letter Regarding 2000 Series*; Tekmar Company, Cincinnati, Ohio (Apr., 1992).

Sensel, A.K., et al., *Comparison of a Narrow Bore Column with a Cryofocusing Module™ and a Wide Bore Column with Jet Separator for EPA Method 524.2*; 1991 Pittsburgh Conference, Tekmar Company (1991).

Applications News 1992, Newsworthy, No. 04050593, *Theory and Operation of Water Management Methods in Purge–and–Trap Gas Chromatography*; O.I. Analytical, College Station, Texas (1992).

*1996 HP Environmental Solutions Catalog*; Hewlett Packard Company, pp. 1–120 (1995).

*GC Star-CX Series*, Varian (1993).

*External Carrier Module Users' Manual*; O.I. Analytical, College Station, Texas, pp. i–7 (Unknown).

Hewlett–Packard, *PEAK News for Users of Analytical Instrumentation*; United States, No. 1 (1995).

*External Carrier Module*; O.I. Analytical, College Station, Texas (Unknown).

*Varian's 3300 and 3400 Gas Chromatographs*; (Unknown).

Abeel, S.M., et al., Trends in Purge and Trap; Journal of Chromatographic Science, vol. 32 (1994).

*4460A Concentrator System Performance Attributes*; O.I. Analytical, College Station, Texas (Unknown).

O.I. Analytical, Application Note 05181195, *Cycle Time as a Productivity Factor in Purge–and–Trap Analysis*; O.I. Analytical, College Station, Texas (Unknown).

Snelling, R.D., et al., *A New Purge and Trap Sample Concentrator Optimized for Low Desorb Flow Operation* O.I. Analytical, College Station, Texas (Mar. 2, 1996).

Riga, T.J., *Low Level Analysis of 524.2 Analytes Using a 3000 Purge and Trap and a Varian Direct Split Interface*; TekNOTE, Tekmar Company, Cincinnati, Ohio (1994).

Hollis, J.S., et al., *Method 524.2 By Capillary Direct Via The Split/Splitless Injection Port on the Hewlett–Packard 5890/5971 GC/MS*; 220P (Unknown).

Neal, B., *EPA Volatiles Analysis Using Narrow Bore Capillary Columns*; Hewlett Packard Company (Unknown).

*EPA Method 524.2 by capillary direct split mode using the HP 5972A Mass Selective Detector (MSD)*; Hewlett–Packard Applications Group, MS Applications Guide, HP 5972A, MS 94–5 (1994).

Bayer, C.W., et al., Sampling and analysis techniques for trace volatile organic emissions from Consumer Products; Journal of Chromatographic Science, 26:168–173 (1988).

Ashley, D.L., et al., Determining volatile organic compounds in human blood from a large sample population by using purge and trap gas chromatography/mass spectrometry; Anal. Chem. 64:1021–29 (1992).

Sauer, T.C., Volatile liquid hydrocarbon characterization of underwater hydrocarbon vents and formation waters from offshore production operations; Enivron. Sci. & Technol., 15(8):917–923 (1981).

Hall, P.M., Analysis of aldehydes desorbed from an aluminum surface using dynamic headspace gas chromatography—mass spectrometry; LC–GC 7(1):52–57 (Jan. 1989). *Organic Volatile Impurities*; Pharmacopeial Forum 19(2):4917–20 (Mar./Apr. 1993).

Page, B.D., et al., Survey of Bottled Drinking Water Sold in Canada. Part 2. Selected Volatile Organic Compounds; Journal of AOAC Int'l., vol. 76, No. 1, pp. 26–31 (1993).

Eichelberger, J.W., et al., Method 524.2, Revision 3.0, *Measurement of Purgeable Organic Compounds in Water by Capillary Column Gas Chromatography/Mass Spectrometry*; Environmental Mon. Sys. Lab., pp. 285–323 (1989).

Method 502.2.: *Volatile Organic Compounds in Water by Purge and Trap Capillary Column Gas Chromatography With Photoionization and Electrolytic Conductivity Detectors in Series*; (Sep. 1986).

Method 524.1: *Volatile Organic Compounds in Water by Purge and Trap Gas Chromatography/Mass Spectrometry*; pp. 56–81.

Method 5030B, Revision 2: *Purge–And–Trap for Aqueous Samples*; pp. 1–21, Revision 2 (Jan. 1995).

Method 503.1.: *Volatile Aromatic and Unsaturated Organic Compounds in Water by Purge and Trap Gas Chromatography*; pp. 28–55 (Unknown).

Method 8020: *Aromatic Volatile Organics*; pp. 8020–1–8020–13, Revision 0 (Sep. 1986).

Method 8020A, Revision 1: *Aromatic Volatile Organics by Gas Chromatography*; pp. 8020A–1–8020A–14 (Sep. 1994).

*Purgeable Aromatics—Method 602*; Environmental Monitoring and Support Laboratory, EPA Test Method, U.S. Environmental Protection Agency, Cincinnati, Ohio, pp. 602–1–602–10 (Jul. 1982).

*Acrolein and Acrylonitrile—Method 603*; Environmental Monitoring and Support Laboratory, EPA Test Method, U.S. Environmental Protection Agency, Cincinnati, Ohio, pp. 603–1–603–8 (1982).

*Method 8030: Acrolein, Acrylonitrile, Acetonitrile*; pp. 8030–1–8030–10, Revision 0, (Sep. 1986).

*Supleco Catalog*; Supelco, Inc., Bellefonte, PA, pp. i–960 (1995).

*VICI Valco Instruments Co., Inc. Catalog*; Valco Instruments Co., Inc., Houston, Texas, pp. 2–60 (1991).

*Guide to Environmental Analytical Methods, 2d Edition*; O.I. Analytical, College Station, Texas, pp. iii–F–1 (1992). *Purge and Trap Comparisions*; O.I. Analytical, College Station, Texas, pp. 1–2 (1996).

Snelling, R.D., et al., Abstract No. 022P, *A New Purge–And–Trap Sample Concentrator Optimized for Low Desorb Flow Operation*; presented at 1996 Technical Program, Pittsburg Conf. 96, Session 165, p. 20 (Mar. 3, 1996).

Snelling, R.D., et. al., Abstract No. 1125, *Detection Limits for Purge and Trap–Gas Chromatography Spectrometry Using a Purge–And–Trap Sample Concentrator Optimized for Capillary Column Flow Rates*; presented at 1996 Technical Program, Pittsburg Conf. '96, Session 136, p. 64 (Mar. 3, 1996).

*Hypodermic Size Tubing, Section III, The MicroGroup Porducts and Services Specifiers Guidebook*; All–Tube Corporation, Medway, MA, pp. 27, 67, 30, 7119, 24 (Unknown).

CDS 330 GC–Sample Concentrator, *Glass–Lined Option Improves and Simplifies GC Analysis of Polar and Labile Compounds*; Chemical Data Systems, Oxford, PA (1985).

Environmental Analysis, Application Report No. 223, *Recent Advances in Volatile Organic Analyses Using Gas Chromatography/Mass Spectrometry: Drinking Water Analyses on the INCOS™ 500*, by Michael T. Barber, Field Application Chemist, Finnigan MAT; pp. 1–11, 1990.

Environmental Analysis, Technical Report No. 616, *Efficient Water Removal for GC/MS Analysis of Volatile Organic Compounds with Tekmar's Moisture Control Module™*, by Eric Johnson, Finnigan MAT and Alan Madden, Tekmar Company, pp. 1–4, 1990.

The Pittsburgh Conference in New York, Mar. 5–9, 1990, *Advances in EPA Method 524.2 Purge and Trap Analysis*, by Bernie B. Bernard, No. 43, 1990.

The Journal of Chromatography, vol. 537, Nos. 1+2, Adsorption/thermal desorption for the determination of volatile organic compounds in water, by Michael E. Rosen and James F. Pankow, pp. 321–328, 1991.

*The Development of Adsorption/Thermal Desorption for the Determination of Trace Levels of Volatile Organic Compounds in Groundwater*, by Michael E. Rosen in a dissertation submitted to the faculty of the Oregon Graduate Center in partial fulfillment of the requirements for the degree Doctor of Philosophy in Environmental Science and Engineering, Jan. 1988, pp. vi–70 and 245–252.

*CARBOFRIT™ Inlet Liner Inserts: An alternative to glass wool packings for split and splitless injection liners*. The Restek Advantage; Restek Corporation, Bellefonte, PA, pp. 1–16 (Spring 1996).

MICROTRAP SAMPLE CONCENTRATOR AND METHODS OF USE

BACKGROUND OF THE INVENTION

1 Field of the Invention

Purge and trap sample concentrators were developed to improve the sensitivity of analysis of volatile organic compounds in water samples. Purge and trap sample concentrators were first developed when packed columns were used in most gas chromatographs. Packed columns typically operate at carrier gas flow rates of fifteen to thirty milliliters per minute. The early sample concentrators were developed to desorb efficiently at these flow rates, and the trap dimensions specified in the US EPA methodologies were designed for packed column use.

The analysis of volatile organic compounds (VOCs) by purge and trap is perhaps the most widely employed method of trace analysis in environmental organic chemistry. This is because it is applicable to a wide variety of analytes in practically any sample matrix and is, to date, still unsurpassed in method sensitivity.

Purge and trap has been adapted to a variety of matrices: the analysis of VOCs in human blood, (D. L. Ashley, M. A. Bonin, F. L. Cardinali, J. M. McCraw, J. S. Holler, L. L. Needham, and D. G. Patterson; Determining volatile organic compounds in human blood from a large sample population by using purge and trap gas chromatography. *Anal. Chem.* 64:1021–29 (1992); consumer products, e.g., floor coverings and air deodorizers (C. W. Bayer, M. S. Black, and L. M. Galloway; Sampling and analysis techniques for trace volatile organic emissions from consumer products. *J. Chromatogr. Sci.* 26:168–73 (1988), offshore waste gas in crude oil production (T. C. Sauer; Volatile liquid hydrocarbon characterization of underwater hydrocarbon vents and formation waters from offshore production operations. *Environ Sci. Technol.* 15(8):917–22 (1981), and on surfaces (P. M. Hall; Analysis of aldehydes desorbed from an aluminum surface using dynamic headspace gas chromotography—mass spectrometry. *LC-GC* 7(1):52–57 (1989). The technique is also used for the determination of residual solvents in pharmaceutical products (U.S.P. Method 467: Organic Volatile Impurities. *Pharmacopeial Forum* 19(2):4917–20 (1993), and has recently been suggested for the analysis of bottled drinking water (B. D. Page, H. B. S. Conacher, J. Salminen, G. R. Nixon, G. Riedel, B. Mori, J. Gagnon, and R. Brousseau; Survey of bottled drinking water sold in Canada. Part 2. Selected volatile organic compounds. *Assoc. Off. Anal. Chem. Int.* 76(1):26–31 (1993). Undoubtedly, the analysis of priority pollutants in water is still the most common application of this technique. Purge and trap is required for the determination of VOCs in public drinking water supplies (Method 524-2: Volatile Organic Compounds in Water by Purge and Trap Capillary Column Gas Chromotography—Mass Spectrometry. U.S. Environmental Protection Agency, U.S. Government Printing Office, Washington, D.C., August, 1986; Method 502.2: Volatile Organic Compounds in Water by Purge and Trap Capillary Column Gas Chromatography with Photoionization and Electrolytic Conductivity Detectors in Series, Revision 2.0 U.S. Environmental Protection Agency, Office of Research and Development, Cincinnati, Ohio, December, 1988), as well as a variety of environmental matrices tested under the U.S. Environmental Protection Agency (EPA) Contract Laboratory Program (CLP).

Many advances and trends in volatiles instrumentation can be traced over the last two decades, but the initial technique was based around simple hardware. The intent was that as legislation requiring the testing of VOCs in water was enacted, it would be relatively inexpensive and easy to incorporate the methodology into the analytical laboratory routine. Since its conception, the purge and trap technique has survived almost constant refinement and adaptation.

1. OVERVIEW OF STANDARD PURGE AND TRAP SAMPLE CONCENTRATOR

Typically with a standard purge and trap sample concentrator, as shown in FIG. 1, the sample concentration cycle involves the steps of purge, desorb, and bake as described above. During purge, the analyte stream flows from sparge vessel 13 (See FIG. 1) through water management device 10 to trap 11, which is at a cool temperature (approximately 20 degrees C.). During desorb, the trap is heated (to approximately 180 degrees C.) and back-flushed with carrier gas. The analyte stream flows from the trap 11 to the water management device and then to the GC or MS. During bake, both the trap and the water management device are heated to approximately 240 degrees C. Dry gas is introduced to the system to move water vapor out of the water management device and trap through vent 14.

More specifically, FIG. 1 diagrams the purge (extraction; FIG. 1A), desorb (injection; FIG. 1B), and the bake step (FIG. 1C) of the purge and trap technique. To begin the analysis, an aliquot of the sample is introduced into a glass sparging container (vessel). In most cases, a 5-ml sample volume provides adequate sensitivity, but when more sensitivity is required, a 25-ml volume may be needed to achieve the minimum detection limits (MDLs) specified in some methods. The sample is purged with either ultrapure helium or nitrogen (greater than 99.998%) at a specified flow rate, temperature, and time (FIG. 1A). This extracts the volatile analytes from the sample matrix and transfers the volatile components to an ambient temperature trap (i.e., typically, a short, ⅛-inch outer diameter packed column) containing as few as one to as many as four different adsorbents.

Following the purging and trapping step, the volatile analytes are thermally desorbed (injected) onto the gas chromatographic (GC) column (FIG. 1B). This is accomplished by rapidly heating the helium-swept trap to a sufficient temperature to transfer the analytes in a narrow injection band (in an attempt to simulate the effect of a direct syringe injection). The chromatographic separation employing columns designed specifically for the analysis then begins. The most commonly used detectors are mass spectrometers (MS) or photoionization detectors (PIP) coupled in series with electrolytic conductivity detectors (ELCD).

The final step in the analysis is the preparation of the sample concentrator for the next sample. This involves baking the adsorbent trap at an elevated temperature with flow through the trap in the reverse direction of the purge/ extraction flow (FIG. 1C). The bake step and the chromatographic separation are, for the most part, carried out simultaneously.

2. SAMPLE CONCENTRATORS

Sample concentrators are used in purge and trap, headspace, and thermal desorption gas chromatography ("GC") analysis. Purge and trap GC technique has been used for analyzing volatile organics in water since approximately the early 1970's. In 1987, the U.S. Environmental Protection Agency ("EPA") promulgated national primary drinking water regulations for certain volatile organic chemicals ("VOCs"). The EPA also proposed maximum contamination levels for eight volatile organic chemicals. These regulations require the use of the purge and trap GC technique. In addition to the eight regulated volatile organic chemicals, the EPA also promulgated monitoring requirements for an additional 84 synthetic volatile organic chemicals and two internal standards.

One of the EPA methods is 502.2, a purge and trap capillary-column GC method using a photoionization detector and an electrolytic conductivity detector joined in series. A second method is method 524.2, a purge and trap capillary-column GC-MS method for determination of organic volatiles in drinking water.

Tentative identifications are confirmed by analyzing standards under the same conditions used for samples, and comparing results and GC retention times. Additional confirmatory information can be gained by comparing the relative response from the two detectors. Each identified component is measured by relating the response produced for that compound to the response produced by a compound that is used as a internal standard. For absolute confirmation, the gas chromatography/mass spectrometry (GC/MS) determination according to method 524.1 or method 524.2 may be used.

Under EPA specifications, the glass purging device must be designed to accept five to twenty-five ml. samples with a water column at least 5 cm. deep. Gaseous volumes above the sample are kept to a minimum to reduce "dead volume" effects. The purged gas passes through the water column at least 5 cm. deep. Gaseous volumes above the sample are kept to a minimum to reduce "dead volume" effects. The purged gas passes through the water column as finely divided bubbles.

The OI Model #4460A Sample Concentrator manufactured by OI Analytical (OI) of College Station, Tex., is an example of a standard purge and trap or sample concentrator device. The Model #4460A is a microprocessor controlled device that stores method 502.2 and 524.2 operating conditions as default parameters. Operating conditions may be changed by the user to accommodate other types of purge and trap analysis.

In addition to purge and trap methods and analyses, sample concentration gas chromatography is used in headspace analysis of liquids and solids, and in thermal desorption analysis of air tube samples. Headspace and thermal desorption techniques are not only used for environmental analyses, but also for clinical and industrial applications.

During all sample concentration GC analysis, some amount of water is purged from the sample and caught in the trap along with the compounds of interest. This was a problem encountered in the prior art. A typical rate of water transfer is 1 microliter per minute of purge time. Without any water management system, during the 11-minute purge time required by method 502.2, approximately 10 to 11 microliters of water are transferred to the trap.

Typically, the methods described above call for a four minute desorb period, which is represented on the GC or MS plot as the first four minutes of run time. Generally, few, if any, analytes show up on the GC or MS during approximately the first four minutes. However, methane and water begin appearing during that period. After the four minute desorb period, water continues to appear, obscuring the analytes of interest.

Water continues to be transferred from the trap to the GC during the remainder of the run time, or will be limited to approximately the first six or seven minutes of run time, depending on various factors. In general, if water transfer time is reduced, there is greater distortion of results (represented graphically as a "higher" plateau) during that reduced time period. If the water transfer time is extended, the distortion will continue further during the GC run time. Regardless of the length of time during which water transfer occurs, it has a tendency to obscure the analytes of interest.

In the OI Analytical Model #4460A sample concentrator, the desorption of water vapor onto the GC column is reduced by a water management system that utilizes rapid trap heating at 800° C. per minute coupled with an expansion/condensation chamber that allows only 1.1 microliters of water vapor to desorb onto the GC column. Due to this water management system, over 90% of the trapped water can be rejected. When the chamber is at 35° C., approximately 1.1 microliters of water vapor are desorbed onto the GC column during the four minute desorb period. These systems also reduce water-activated deterioration of the ELCD nickel reaction tube and the subsequent loss of response to certain compounds.

As another alternative to eliminate water vapor transfer to the GC columns, OI Analytical's Anhydrator reduces water transfer to the GC column to less than 0.004 microliters per minute. The Anhydrator consists of Nafion tubing available from Perma-Ture Corporation. The Anhydrator has disadvantages and problems including irreversible loss of polar analytes such as acetone and methanol, which are removed along with the water.

The inventions of U.S. Pat. Nos. 5,250,093, 5,470,380, 5,358,557, and 5,582,633 as well as a co-pending U.S. patent application, U.S. Ser. No. 08/559,721 (filed Nov. 15, 1995), herein incorporated by reference, overcome the above mentioned problems and disadvantages by providing a water management system wherein the water vapor pressure and temperature behavior. The amount of water removed is more than can be accounted for by simple condensation.

These inventions include a water management device having a passage through which VOCs and water vapor pass, the passage designed to remove water vapor by swirling action on the stream. The passage has additional surface area, such as an internally threaded configuration, without significantly increasing the dead volume, and without temperatures as low as the prior art.

These inventions include a process of adjusting the temperature of the water management device during the purge, desorb, and bake cycle. During the purge step, the device reaches a temperature somewhat higher than the trap temperature, to reduce condensation before the analyte stream reaches the trap. Just prior to desorb, the water management device is cooled further, approaching ambient room temperature, to remove water vapor from the analyte stream being desorbed from the trap to the GC.

These inventions are primarily intended for use with a back-flush system, but also may be used with a fore-flush system. (See FIG. 16). When used in a back-flush system, the first end of the device is the outlet during purge and the inlet during desorb, and the second end is the inlet during purge and the outlet during desorb. The removal of water is intended to take place primarily during the desorb step.

3. CURRENT STATUS OF STANDARD PURGE AND TRAP SAMPLE CONCENTRATORS

The current generation of purge and trap sample concentrators were originally developed for use with gas chromatographs equipped with packed columns and were designed to operate with desorption flow rates optimized for packed columns. These columns were typically operated at a carrier gas flow rate of 20 to 30 ml/min. The trap dimensions which are standard for purge and trap sample concentrators are designed to operate efficiently at these flow rates. In the time period since purge and trap sample concentrators were first introduced, a major shift away from the use of packed columns has taken place. The majority of gas chromatographs are currently operated with capillary columns, and packed columns are now used primarily for a few specialized applications. Modern capillary columns operate at much lower flow rates than packed columns, with typical flow rates ranging from 0.7 ml/min. for a 0.2 mm column to 10 ml/min. for a 0.53 mm column.

The difference in optimum flow desorption rates for the trap and the column compromises analytical performance. The use of megabore columns (0.53 mm id) allows high enough desorption flow to efficiently desorb analytes from the trap in a tightly focused band, but these columns have a relatively low chromatographic efficiency, required long columns and extended run times for good chromatographic performance. The use of more efficient, narrower bore columns (0.2 to 0.32 mm id) requires either a low desorption flow rate through the trap which results in a broad, poorly focused analyte band at the head of the column, a high desorption flow through the trap with splitting of the sample stream prior to the head of the column which adversely affects detection limits, or the use of cryogenic focusing device to focus the analytes at the head of the column after a long desorption at a low flow rate.

The difference in flow rates for optimum performance is a major problem when a mass spectrometer is used as the detector for a gas chromatograph connected to a purge and trap sample concentrator. Mass spectrometers operate most efficiently at flow rates of less than one ml/min., and traps are desorbed most efficiently at a flow rate of 15 to 30 ml/min. Thus, the desorption flow must be split either before the analytes are introduced onto the column, or at the end of the column prior to introduction into the mass spectrometer. In either case, the splitting of the analytes reduces the sensitivity of the technique.

The most commonly used methods use either a splitless or split injection technique. The splitless technique used with a narrow bore capillary column typically requires cryofocusing. This method is suited for trace analysis but one is limited to a small linear working range, lower sample capacity and cryogenics are needed. Also, a loss of sensitivity may occur depending on the split ratio. Furthermore, standard split/splitless GC injectors were designed to accommodate the higher flow rates. Another limitation is the cost incurred for purchasing some type of split interface.

A purge and trap-mass spectrometer (MS) interface that has received a great deal of attention recently is referred to as a capillary "split injection" interface. First developed in 1989, this interface eliminated both cryofocusing and jet separation as requirements for interfacing a purge and trap to an MS. Briefly, a total gas flow (variable) is supplied through the sample concentrator's six-port valve from a constant flow controller. This gas is used to desorb the analyte from the trap to the injector via the sample concentrator's heated transfer line. The transfer line is connected via an LDV union directly into the carrier gas inlet of a split GC injector. With a 0.25 mm id (or smaller) capillary column connected to the inlet, 0.5-1.5 ml/min of column flow is allowed into the column, and the remainder is diverted to a variable split vent. Using this system, analytes are desorbed from the trap under high gas flow but the flow to the column is reduced to the optimum for the chromatographic separation.

Thus, the current generation of purge and trap sample concentrators is still designed to operate with desorption flow rates optimized for packed columns. These desorption flow rates are also appropriate for 0.53 millimeter inside diameter or megabore columns. Packed columns are becoming functionally obsolete except for specialized applications, and the US EPA has proposed removal of all packed column methods from the SW-846 manuals. Megabore columns are widely used for the analysis of volatile organic compounds, but the use of these columns requires compromises.

Limitations of the Standard Purge and Trap Systems, e.g., Tekmar 3000

1. Trap heating rate is limited by indirect heat from a heating sleeve or jacket around trap.

2. Trap heats sample up to 225°0 C. at 575° C./min., which may be insufficient to desorb at 1 cc/min.

3. Tekmar 3000 does not have a heating rate that could benefit from a low volume trap.

4. The temperature is poorly controlled (often overshoots) at the high temperatures which are now required by many of the new sorbents.

Attempts to Improve Standard Purge and Trap System

A product called External Carrier Module or "ECM" has been developed by OI Analytical in an attempt to improve the purge and trap system.

A. "ECM Introduction"

The External Carrier Module ("ECM") is used in conjunction with the OI Model #4460A Sample Concentrator and a gas chromatographic system. The ECM was designed for use on systems that have capillary columns with low flow rates (~1 ml/min). The ECM consists of a pressure regulator, flow controller, and two valves that work together to deliver a burst of pressure to the trap in the 4460A at the beginning of the Desorb phase. This pressure burst allows trapped compounds to rapidly desorb onto the gas chromatographic column. The ECM is electrically connected to a gas chromatograph (GC) and is controlled manually from the GC's front panel or automatically by the GC's time program.

B. "ECM Operation"

The ECM provides a burst of pressure that aids in desorbing trapped compounds onto a gas chromatographic capillary column. When in the burst mode, the gauge on the front panel displays the burst pressure. The burst pressure can be adjusted using the burst pressure regulator knob. Rough carrier flow is set by connecting a flowmeter to the vent tube on the rear panel of the ECM and adjusting the column flow knob on the front panel when ECM is in burst mode. Once flow is set and 24 volts is supplied to the unit, the valves switch, putting the unit into burst mode, which delivers the burst pressure to the trap of the 4460A. The compounds then rapidly desorb onto the gas chromatographic column. The burst should last approximately three seconds. The ECM can be manually or automatically controlled.

C. "ECM Was NOT Successful"

For many different reasons, the ECM as designed and constructed, did not solve the following problems:

1. With columns of <0.32 mm diameter, the decay of the burst pressure spike was too long due to the high backpressure of the column. ECM worked well only with 0.32 mm and larger columns.

2. Burst time duration was critical and time control sensitivity provided by the GC was not always adequate.

3. THE TREND IS MOVING TOWARD IMPROVING/ CHANGING THE PURGE AND TRAP SAMPLE CONCENTRATORS

The trend now is toward faster analysis and this requires the use of shorter GC columns, preferably with a narrower bore to maintain resolution. When narrower bore columns are used shorter columns may be used without losing resolution. The narrow bore columns typically have a much shorter run time than a megabore column of the same resolving power, increasing instrument productivity. The narrow bore columns operate at much lower flow rates than packed columns or megabore columns. Typical flow rates range from one to three milliliters per minute. At these flow rates the flow through a standard trap is too low for an efficient desorption. It is necessary to either split the sample stream or refocus the analytes cryogenically at the head of the column. Splitting the sample stream decreases the sensitivity of the analysis. Cryogenic focusing requires more equipment and a long desorption time at a low flow rate.

In general, the standard sorbent trap is a tube typically at least 25 cm. long and having an inside diameter of at least 0.105 inches. The trap contains certain sorbent materials which the EPA has specified as 2,6-diphenylene oxide polymer, silica gel, and coconut charcoal. The EPA regulations specify the ratios of the adsorbent material. The desorber must be capable of rapidly heating the trap to 180° C.

U.S. EPA position on traps is changing. Method 5030B in the Third Update to the SW-846 manual states that a 12"×⅛" trap was used in developing the method, but the language requiring the trap to be at least 12" long with an inner diameter of at least 0.105" has been dropped. In addition, the new method allows the use of alternative sorbents and desorption temperatures and times as long as the results are equivalent to the standard trap results.

SUMMARY OF THE INVENTION

The new purge and trap sample concentrator of this invention was designed to optimize performance at low desorption flow rates (one to three milliliters per minute). The concentrator uses sorbent materials and flow paths sized for optimum performance at the flows required for the use of narrow bore capillary columns. This allows for faster chromatography while maintaining high resolution. The sample concentrator will also accept conventional traps containing standard sorbents for use with megabore columns.

The new purge and trap sample concentrator claimed in this invention was modified to operate at narrow bore capillary column flow rate. By choosing the proper sorbent and designing the flow path for lower rates, a system was developed to introduce the sample to the head of the column in a tightly focused band using a one milliliter per minute flow during the desorb step. Transferring all the sample to the column improves the detection limits when a mass spectrometer is used as the detector. Typical detection limits using the modified purge and trap sample concentrator are less than 20 parts per trillion. The analytes are purged or drawn from a sample derived from the group consisting of water, soil, food, beverage, pharmaceutical products, biological samples, forensic samples, air samples, gaseous samples, polymers, and sediment matrices.

In general, in one aspect, the invention features a microtrap sample concentrator which is useful for concentrating a sample of purged gas containing analytes for delivery to an analytical instrument, including: a) a tube containing at least one sorbent material which retains or traps analytes; where greater than 30% of all trapped analytes are directly delivered to an analytical instrument at a desorption flow rate of one to three cc/min, without splitting or cryogenic focusing the trapped analytes; where delivery of the trapped analytes to the analytical instrument is achieved by passing the trapped analytes through a passage being selectively connectable between the microtrap and the analytical instrument, the passage connected to a vent; where the temperature of the passage is not lower than ambient room temperature; and where the passage is heated by a heating means to a temperature sufficient to vaporize water in the passage and to expel the vaporized water out of the vent.

Implementations of the invention may include one or more of the following features. The passage of the microtrap sample concentrator is configured to impart an angular velocity on the analytes flowing from the microtrap to the analytical instrument. The tube of the microtrap sample concentrator is either hypodermic or instrument grade and has a straight, U-shaped, and coiled shape; the tube is either stainless steel and nickel; the stainless steel tubing may include one of the following: stainless steel Type 304, stainless steel Type 303, stainless steel Type 316, stainless steel Type 416, stainless steel Type 446, and stainless steel Type 326; the nickel tubing may include nickel 200 alloy; the tube size is approximately 10 cm. (4 inches) to 30 cm. (12 inches) long, having an outside diameter in the range of between 0.050 inches and 0.095 inches, having an inside diameter in the range of between 0.045 inches and 0.085 inches. The sorbent materials may include one of the following: 2,6-diphenylene oxide polymer, silica gel (15), coconut charcoal (activated charcoal), activated alumina, Carbopack B, Carbopack C, Carbopack F, Carbosieve S-111, Carboxen 1000, Carboxen 1001, Carbowax 20M, Tenax TA, SP-2100/Chromosorb W AW, SP-2250, SP-1200, SP-1000, Porapak Series (N, P, PS, Q, QS, R, S,T,), Porasil, Porasil B, HayeSep Series (A, B, C, D, N, P, Q, R, S), Durapack n-Octane/Porasil C, Molecular Sieve 5A, Molecular Sieve 13X, and Molecular Sieve 4A. The microtrap may also include a gas chromatograph comprising a gas chromatograph column as the analytical instrument and the gas chromatograph column may have an inner diameter of less than 0.45 mm. The ID/OD ratio of the tube of the microtrap may include ranges from about 0.085"/0.095" to about 0.045"/0.050"; the ID/OD ratio of the tube may also be about 0.060"/0.065". The inner diameter of the tube of the claimed microtrap may be of such a size that the trap volume per minute at a one cc/min desorption flow rate is between about 2.5 and about 4.5, the linear velocity at a desorption flow rate of one cc/min is between about 0.700 cm/second and about 1.0 cm/second and the heating rate is between about 1200° C./min and about 1800° C./min. For this feature, the ID/OD ratio of the tube may range from about 0.085"/0.095" to about 0.045"/0.050"; the ID/OD ratio of the tube is about 0.060"/0.065". This microtrap includes that the analytes are purged or drawn from a sample derived from the group consisting of water, soil, food, beverage, pharmaceutical products, biological samples, forensic samples, air samples, gaseous samples, polymers, and sediment matrices. This microtrap also features that greater than 90% of all trapped analytes are directly delivered to the analytical instrument at a desorption flow rate of one to three cc/min, without splitting or cryogenic focusing the trapped analytes; that 100% of all trapped analytes are directly delivered to the analytical instrument at a desorption flow rate of one to three cc/min, without splitting or cryogenic focusing the trapped analytes.

In general, in another aspect, the invention features a method of delivering greater than 30% of concentrated analytes to an analytical instrument including: a) purging or drawing an analyte stream from a sparge vessel containing a sample; b) passing the purged analytes through a first passage connecting the sparge vessel to a microtrap where the analytes associate with at least one sorbent material contained within the microtrap; and c) desorbing the analyte stream from the microtrap at a desorption flow rate of one to three cc/min and directly passing greater than 30% of the desorbed analyte stream through a second passage from the microtrap to an analytical instrument, without first splitting or cryogenically focusing the analyte stream; where the temperature of the second passage is not lower than ambient room temperature; and where the second passage is heated by a heating means to a temperature sufficient to vaporize water in the passage and to expel the vaporized water out of a vent.

Implementations of the invention may include one or more of the following features. The method including that the second passage is configured to impart an angular velocity on the analytes flowing from the microtrap to the analytical instrument; the microtrap of the method including a tube containing at least one sorbent material which retains or traps the analytes. The tube of the microtrap where the tube is of hypodermic or instrument grade and wherein the shape of the tube is selected from the group consisting of straight, U-shaped, and coiled; where the tube is selected from the group consisting of stainless steel and nickel; where the stainless steel may be one of the following types: stainless steel Type 304, stainless steel Type 303, stainless steel Type 316, stainless steel Type 416, stainless steel Type 446, and stainless steel Type 326; where the nickel is nickel 200 alloy; where the tube is approximately 10 cm. (4 inches) to 30 cm. (12 inches) long, having an outside diameter in the range of between 0.050 inches and 0.095 inches, having an inside diameter in the range of between 0.045 inches and 0.085 inches. The sorbent contained within the microtrap may be one of the following: 2,6-diphenylene oxide polymer, silica gel (15), coconut charcoal (activated charcoal), activated alumina, Carbopack B, Carbopack C, Carbopack F, Carbosieve S-111, Carboxen 1000, Carboxen 1001, Carbowax 20M, Tenax TA, SP-2100/Chromosorb W AW, SP-2250, SP-1200, SP-1000, Porapak Series (N, P, PS, Q, QS, R, S,T,), Porasil, Porasil B, HayeSep Series (A, B, C, D, N, P, Q, R, S), Durapack n-Octane/Porasil C, Molecular Sieve 5A, Molecular Sieve 13X, and Molecular Sieve 4A. The analytical instrument used in the method may be a gas chromatograph comprising a gas chromatograph column and the gas chromatograph column may an inner diameter of less than 0.45 mm. The ID/OD ratio of the tube may range from about 0.085"/0.095" to about 0.045"/0.050"; the ID/OD ratio of the tube may be about 0.060"/0.065". The tube of the microtrap may have an inner diameter such that the size that the trap volume per minute at a one cc/min desorption flow rate is between about 2.5 and about 4.5, the linear velocity at a desorption flow rate of one cc/min is between about 0.700 cm/second and about 1.0 cm/second and the heating rate is between about 1200° C./min and about 1800° C./min. For this tube, the ID/OD ratio of the tube ranges from about 0.085"/0.095" to about 0.045"/0.050"; the ID/OD ratio of the tube is about 0.060"/0.065". The method features that the analytes are purged or drawn from a sample derived from the group consisting of water, soil, food, beverage, pharmaceutical products, biological samples, forensic samples, air samples, gaseous samples, polymers, and sediment matrices. For this method, greater than 90% of all trapped analytes are directly delivered to the analytical instrument at a desorption flow rate of one to three cc/min, without splitting or cryogenic focusing the trapped analytes; 100% of all trapped analytes are directly delivered to the analytical instrument at a desorption flow rate of one to three cc/min, without splitting or cryogenic focusing the trapped analytes.

In general, in another aspect, the invention features an apparatus for removal of water from analytes being purged from a sparge vessel to a microtrap and desorbed from the microtrap to an analytical instrument, including: (a) a purge means or a draw means for purging or drawing the analytes from a sparge vessel and passing the purged analytes through a first passage connecting the sparge vessel to a microtrap; (b) desorbing means for desorbing the analytes from the microtrap and passing the desorbed analytes through a second passage from the microtrap to an analytical instrument, the second passage being configured to impart an angular velocity on the analytes flowing from the microtrap to the analytical instrument, and wherein the temperature of the second passage is not lower than ambient room temperature; and (c) heating means for heating the second passage to a temperature sufficient to expel water vapor from the passage through a vent.

Implementations of this apparatus may include one or more of the following features. The second passage of the apparatus may impart an angular velocity on the analyte stream by causing the analyte stream to flow in a helical path through the second passage during use of the desorbing means; the second passage may impart an angular velocity on the analyte stream by causing the analyte stream to flow in a cylindrical path through the second passage during use of the desorbing means; the second passage may be thermally isolated from the microtrap; a fan for cooling the second passage may be used; the analytes may flow through the second passage in opposite directions during purging and desorption; the second passage may retain enough heat during purging to substantially prevent condensation of water in the second passage; a heating cartridge and thermocouple may be used for heating the second passage; the second passage may impart angular velocity on the analyte stream by spiraling the analyte stream during use of the desorbing means. The apparatus also includes a microtrap including a tube containing at least one sorbent material which retains or traps the analytes; where greater than 30% of all trapped analytes are directly delivered to an analytical instrument at a desorption flow rate of one to three cc/min, without splitting or cryogenic focusing the trapped analytes. The tube of the microtrap may be of hypodermic or instrument grade and may be U-shaped, straight, or coiled; the tube may include one of the following: stainless steel and nickel. The stainless steel may be one of the following: stainless steel Type 304, stainless steel Type 303, stainless steel Type 316, stainless steel Type 416, stainless steel Type 446, and stainless steel Type 326. The nickel may be nickel 200 alloy. The tube size is approximately 10 cm. (4 inches) to 30 cm. (12 inches) long, having an outside diameter in the range of between 0.050 inches and 0.095 inches, having an inside diameter in the range of between 0.045 inches and 0.085 inches. The sorbent materials contained within the microtrap may include one of the following: 2,6-diphenylene oxide polymer, silica gel (15), coconut charcoal (activated charcoal), activated alumina, Carbopack B, Carbopack C, Carbopack F, Carbosieve S-111, Carboxen 1000, Carboxen 1001, Carbowax 20M, Tenax TA, SP-2100/Chromosorb W AW, SP-2250, SP-1200, SP-1000, Porapak Series (N, P, PS, Q, QS, R, S,T,), Porasil, Porasil B, HayeSep Series (A, B, C, D, N, P, Q, R, S), Durapack n-Octane/Porasil C, Molecular Sieve 5A, Molecular Sieve 13X, and Molecular Sieve 4A. At least one sorbent material is included in the tube; many sorbent materials may be included in the tube, e.g., six or seven different ones but four is preferred. The tube may have an ID/OD ratio ranging from about 0.085"/0.095" to about 0.045"/0.050"; and the ID/OD ratio of the tube is about 0.060"/0.065". The inner diameter of the tube may be of such a size that the trap volume per minute at a one cc/min desorption flow rate is between about 2.5 and about 4.5, the linear velocity at a desorption flow rate of one cc/min is between about 0.700 cm/second and about 1.0 cm/second and the heating rate is between about 1200° C./min and about 1800° C./min; for this, the ID/OD ratio of the tube ranges from about 0.085"/0.095" to about 0.045"/0.050"; and the ID/OD ratio of the tube is about 0.060"/0.065". The apparatus also features an analytical instrument which may a gas chromatograph comprising a gas chromatograph column; the gas chromatograph column may have an inner diameter of less than 0.45 mm. With this apparatus, greater than 90% of all trapped analytes are directly delivered to the analytical instrument at a desorption flow rate of one to three cc/min, without splitting or cryogenic focusing the trapped analytes; with this apparatus, 100% of all trapped analytes are directly delivered to the analytical instrument at a desorption flow rate of one to three cc/min, without splitting or cryogenic focusing the trapped analytes.

In general, in another aspect, the invention features a microtrap sample concentrator useful for concentrating a sample of purged gas containing analytes for delivery to an analytical instrument, including a tube containing at least one sorbent material which retains or traps analytes; where greater than 30% of all trapped analytes are directly delivered to an analytical instrument at a desorption flow rate of one to three cc/min, without splitting or cryogenic focusing the trapped analytes.

Implementations of the invention may include one or more of the following features. The tube may be stainless steel or nickel; the tube is approximately 10 cm. (4 inches) to 30 cm. (12 inches) long, having an outside diameter in the range of between 0.050 inches and 0.095 inches, having an inside diameter in the range of between 0.045 inches and 0.085 inches.

Definitions

By capillary columns with low flow rates is meant approximately 1 ml/min flow rate.

By GC is meant gas chromatography.

By MS is meant mass spectrometry.

By o.d. is meant outer diameter. For this invention, o.d. and od are used interchangeably.

For the purpose of this invention, cc (cubic centimeter) and ml (milliliter) are used interchangeably.

By i.d. is meant inner diameter. For this invention, i.d. and id are used interchangeably.

By sorbent materials is meant a material or substance that takes up and holds by either adsorption or absorption. For this invention, sorbent, absorbent, and adsorbent are used interchangeably.

By adsorption is meant the adhesion in a thin layer of molecules, e.g., gases or solutes, to the surfaces of solid bodies or liquids in which they are in contact.

By volatile organic chemicals (VOCs) is meant analytes. For this invention, volatile organic chemicals and analytes are used interchangeably.

For the purpose of this invention, limits of detection and minimum detection limits are used interchangeably.
ADVANTAGES OF THE MICROTRAP SAMPLE CONCENTRATOR 1. Microtrap of this invention was designed to allow desorption flow rates at or about 1 cc/min. to a GC system.

A new trap was designed to operate at capillary column flow rates. This new trap was designed to address the need for matching the flow requirements for the trap and the analytical column. The trap was constructed with a smaller inner diameter (id) allowing an efficient desorption at lower flow rates.

This also allowed for improved detection limits for purge and trap gas chromatography/mass spectrometry using the new purge and trap sample concentrator of this invention optimized for capillary column flow rates.

The standard conventional purge and trap systems, e.g., OI #4560, cannot be used at lower flow rates because poor chromatography (peak broadening) would result and therefore be of no benefit.

Also, previously, gas chromatography companies have designed components and features to accommodate only the high flow rates from the standard purge and trap systems.

Thus, the microtrap of this invention (1) allows use of smaller sample volumes while increasing sensitivity of the method because the desorbed gas flow did not need to be split; (2) reduces gas consumed by entire system; (3) maintains adequate linear velocity through trap at low flow rates; (4) reduces sorbent amount required to fill sorbent trap; and (5) reduces surface area and carryover.

2. Microtrap of this invention provides improved performance of purge and microtrap sample concentrator using GC-MS due to: (a) lower detection limits and (b) the elimination of sample splitting.

The efficient desorption at lower flow rates allows the purge and microtrap sample concentrator to be coupled to a GC-MS system without the necessity of splitting the analyte stream. Since the desorption rate in this improved microtrap has been reduced to one to three cc/min, the entire sample can be analyzed by the GC-MS detection system without splitting off or losing 90% of the sample as compared to the conventional traps. Conventional traps have a desorption flow rate of 10 cc/min. However, the GC-MS detection system can only handle a flow rate of 1 cc/min, thus, 9 ccs or 90% of the sample has to be split off or lost from the analysis. Using the microtrap of the instant invention, the direct interfacing of the purge and microtrap sample concentrator to the GS-MS improves the detection limits of the technique. This is especially important in the analysis of drinking water samples, which are much lower in organic content than water samples. Thus, analytes that are lower in concentration are detected with greater sensitivity with the microtrap of this invention.

The microtrap allows use of small bore, capillary columns without splitting the flow from purge and trap to column. Compare the following:

Standard Purge and Trap System, e.g. OI #4560: Requires Splitting:

(1) desorbs at 10 cc/min.; and (2) requires a sample splitting to reduce flow rate from 10 cc/min to 1 cc/min to column with 0.25 diameter; thus, up to 90% of analytes lost (split off).

Microtrap of the Claimed Invention Requires No Sample Splitting:

(1) desorbs at 1 cc/min; and (2) requires NO sample splitting to provide a flow of 1 cc/min to a column of less than 0.25 diameter; thus 100% (complete) transfer of ALL analytes to GC column.

3. Microtrap of this Invention Provides Faster Chromatography with Conventional Detectors Using Smaller Bore Columns.

The use of the microtrap with a gas chromatograph equipped with conventional detectors allows the use of narrower bore columns, increasing the efficiency of the chromatography, sensitivity and the speed of the analysis.

4. Microtrap of this Invention Provides Rapid and Controlled Heating and Cooling Rates The microtrap of this invention heats at greater than 1500° C./min. Compare this to the conventional standard purge and trap system, e.g., OI #4560, which can only heat at approximately 930° C./min and compare this to the Tekmar 3000 which can only heat at approximately 575° C./min. The small trap volume combined with rapid heating rate allows lower flow rate without loss of chromatographic quality. Thus, extremely low thermal mass of the microtrap allows rapid cool down of the trap which shortens cycle (run) time.

5. Microtrap of this Invention Provides Greater Sensitivity and Delivery

The microtrap of this invention allows a smaller sample to be purged with greater sensitivity. Also, the delivery rates are significantly better with the microtrap of this invention.

Compare a 5 cc sample purged onto the microtrap with a 25 cc sample purged onto a standard purge and trap system, e.g., OI#4560. When a 5 cc sample (1ppb concentration; 1 ng/cc=1 ng/ml) is purged (loaded) onto the microtrap of this invention, the microtrap delivers 5 ng of analyte mass to GC column (100% delivery/transfer). In contrast, when a 25 cc sample (1 ppb concentration; 1 ng/cc=1 ng/ml) is purged onto a standard trap, the standard trap only delivers 10% of the 25 ng analyte mass, e.g. only 2.5 ng gets delivered to the GC column because of a 90% split (or 90% loss of sample) required with the standard trap.

6. Microtrap of this Invention Provides Reduced GC Cycle Time

Microtrap reduces GC cycle time: Standard OI #4560 GC column of 0.5 mm diameter requires 45 min. per cycle and the microtrap GC column of 0.25 mm diameter requires only 25 min. per run.

Other features and advantages of the invention will be apparent from the following detailed description, and from the claims.

DETAILED DESCRIPTION

Figure 1:
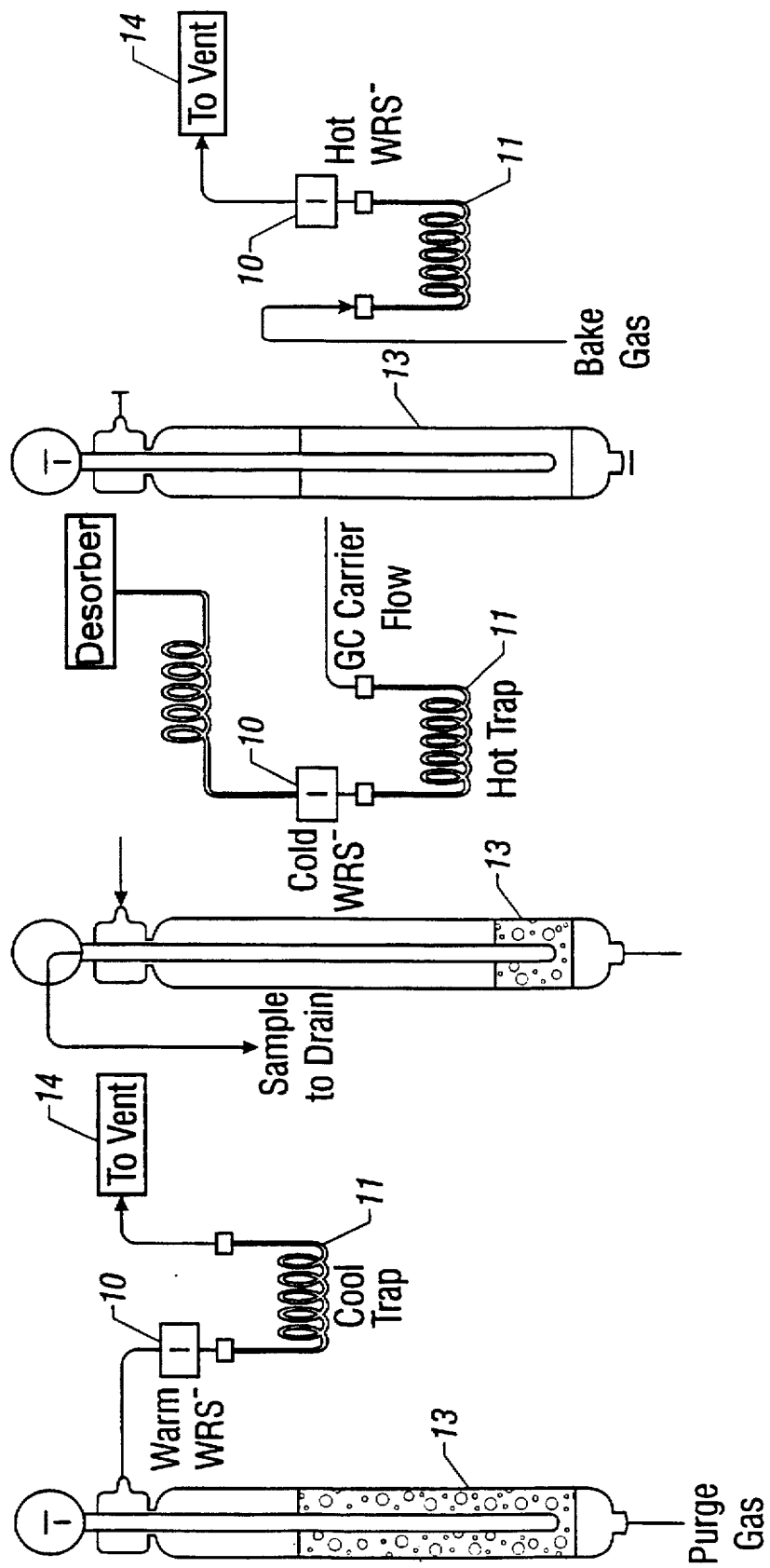
FIG. 1A is a flow diagram illustrating the purge (extraction) step in the purge and trap technique.
FIG. 1B is a flow diagram illustrating the desorb (injection) step in the purge and trap technique.
FIG. 1C is a flow diagram illustrating the bake step in the purge and trap technique.
Figure 1A:
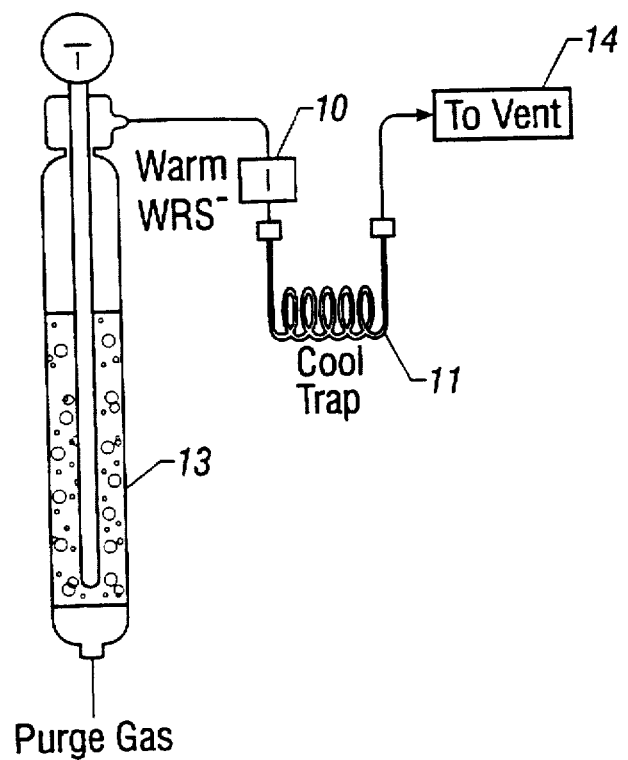
Figure 1B:
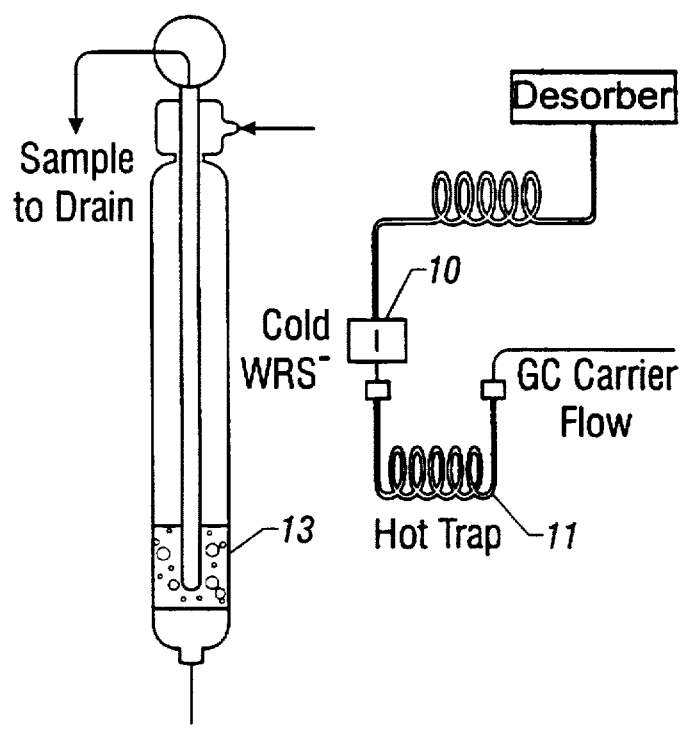
Figure 1C:
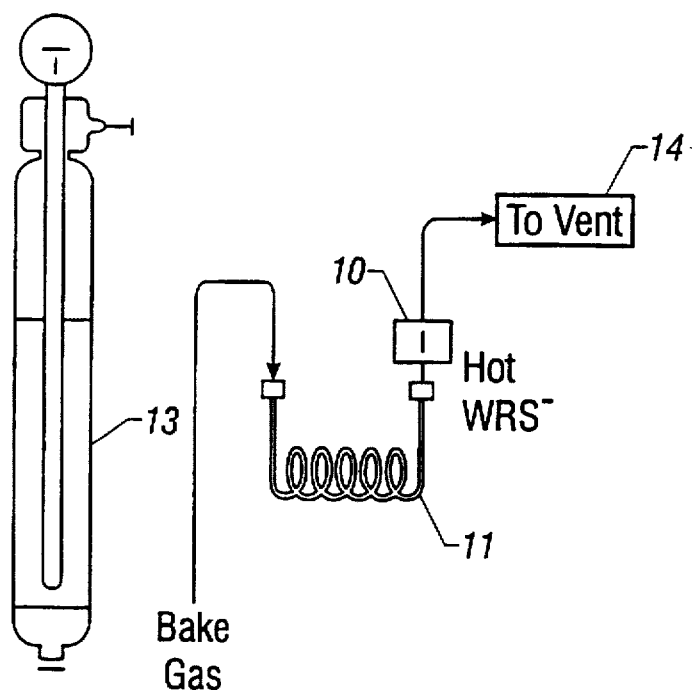

Purge and trap sample concentrators were first developed when packed columns were used in most gas chromatographs. The current generation of purge and trap sample concentrators is still designed to operate with desorption flow rates optimized for packed columns or megabore columns. Packed columns are becoming functionally obsolete, and the U.S. EPA has proposed removal of all packed column methods from the SW-846 manuals. The trend now is toward faster analysis which requires the use of shorter columns, preferably with a narrower bore to maintain resolution.

Purge and trap sample concentrators have been designed to operate at packed column flow rates. The most common columns used with purge and trap sample concentrators are megabore columns with a seven to ten milliliter per minute flow rate. This flow rate is not a problem when using conventional gas chromatography detectors, but it does present problems when a mass spectrometer is used as the detector. Mass spectrometers typically operate with one milliliter per minute flow so in most cases the desorb flow must be split at the inlet port or by using a jet separator prior to the mass spectrometer. The splitting of flow adversely affects detection limits because the majority of the sample is not introduced into the mass spectrometer.

To solve these problems and more, the microtrap of this invention (See Table 1) was designed and constructed to have an outer diameter of 0.065" (1.65 mm), and an inner diameter of 0.059" (1.52 mm), is 14.6 cm in length, and has a volume of 0.26 cc. With the reduced inner diameter and decreased volume, the heating rate for the microtrap sample concentrator was >1500° C./min and the linear velocity of the microtrap, as compared to the standard trap, for a 1 cc/min flow rate, is 2.9 times greater. To optimize the chromotography, the analytes must be transferred from the trap and delivered to the GC column as rapidly as possible. At the low flow rates (1 cc/min) required by the GC/MS method, this transfer efficiency is hampered by the small volume of gas available to effect the transfer. The trap sweep rate (See Table 1) refers to the number of times the trap volume is displaced per unit time. The volume of the microtrap allows 3.84 trap volumes to be displaced per minute, compared to 0.598 volumes to be displaced per minute for the standard trap (both traps desorbed at the standard 1 cc/min flow as dictated by the method). This translates to a volume displacement advantage of a 6.4 times higher (or faster) for the microtrap as compared to the standard trap.

TABLE 1

DIMENSIONS AND DESORPTION RATES OBTAINED WITH A STANDARD TRAP AND THE MICROTRAP OF THIS INVENTION

|  | OD × ID | Length | Trap Volume | Linear Velocity at 1 cc/min | Trap Sweep Rate Trap Vol./min at 1 cc/min Flow Rate | Heating Rate |
| --- | --- | --- | --- | --- | --- | --- |
| Standard Trap | 3.175 mm × 2.667 mm .010 wt | 30.4 cm | 1.67 cc | .313 cm/sec | .598 | OI: 900° C./min Tekmar: 575° C./min |
| Microtrap | 1.65 mm × 1.52 mm .003 wt | 14.6 | .26 cc | .916 cm/sec | 3.846 | >1500° C./min |

Figure 2A:
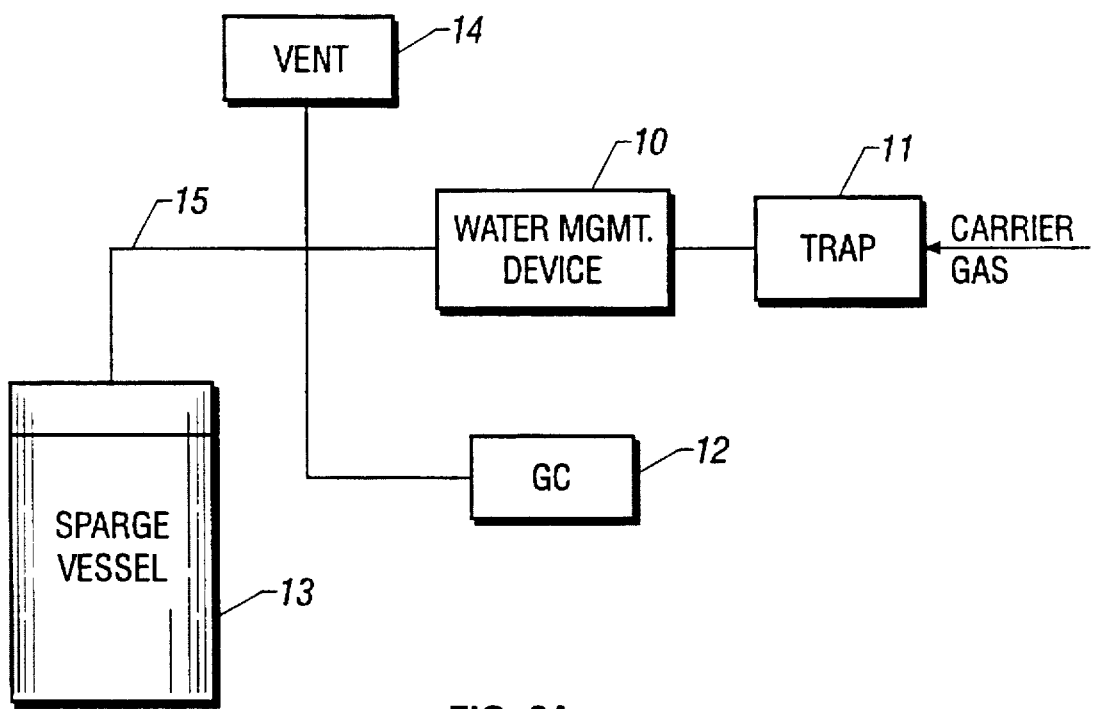
FIG. 2a is a schematic diagram of a standard purge and trap sample concentrator used in a typical sample concentration/gas chromatography system.
Figure 2B:
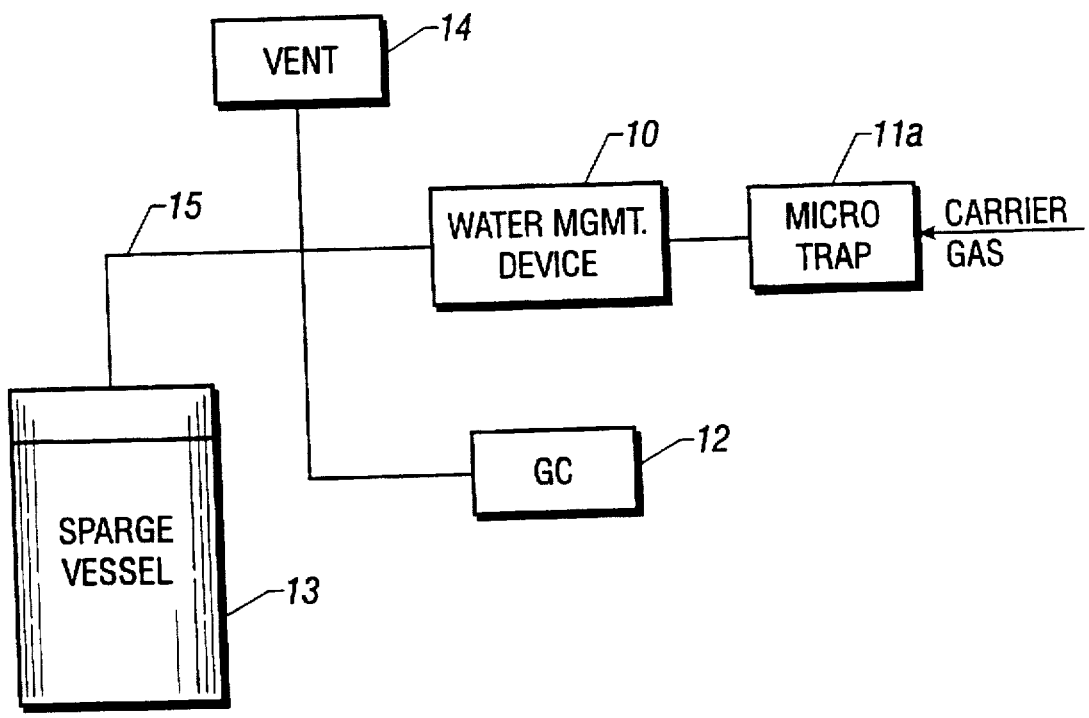
FIG. 2b is a schematic diagram of the microtrap sample concentrator of the present invention and other components used in a typical sample concentration/gas chromatography system.

In a preferred embodiment, a microtrap sample concentrator 11a may be used in place of trap 11, as shown in FIGS. 2b and 2a, respectively. Also shown in FIGS. 2a and 2b are a water management device 10, sparge vessel 13, vent 14, and pneumatic tubing 15 connecting the components.

Typically with a standard purge and trap sample concentrator, as shown in FIG. 1, the sample concentration cycle involves the steps of purge, desorb, and bake as described above. During purge, the analyte stream flows from sparge vessel 13 (See FIG. 1) through water management device 10 to trap 11, which is at a cool temperature (approximately 20 degrees C.). During desorb, the trap is heated and back-flushed with carrier gas. The analyte stream flows from the trap 11 to the water management device and then to the GC column. During bake, both the trap and the water management device are heated to a temperature higher than the desorb temperature. Dry gas is introduced to the system to move water vapor out of the water management device and trap through vent 14.

During this typical sample concentration cycle, the standard sorbent trap is a tube typically at least 25 cm. long and having an inside diameter of at least 0.105 inches (outside diameter of ⅛ inch or 0.125 inches and wall diameter of 0.01 inches). Outside diameter for the standard sorbent trap is in the range of between 0.095 inches and 0.150 inches (0.125 inches optimal), and has an inside diameter in the range of between 0.075 inches and 0.150 inches (0.105 inches optimal).

Figure 3:
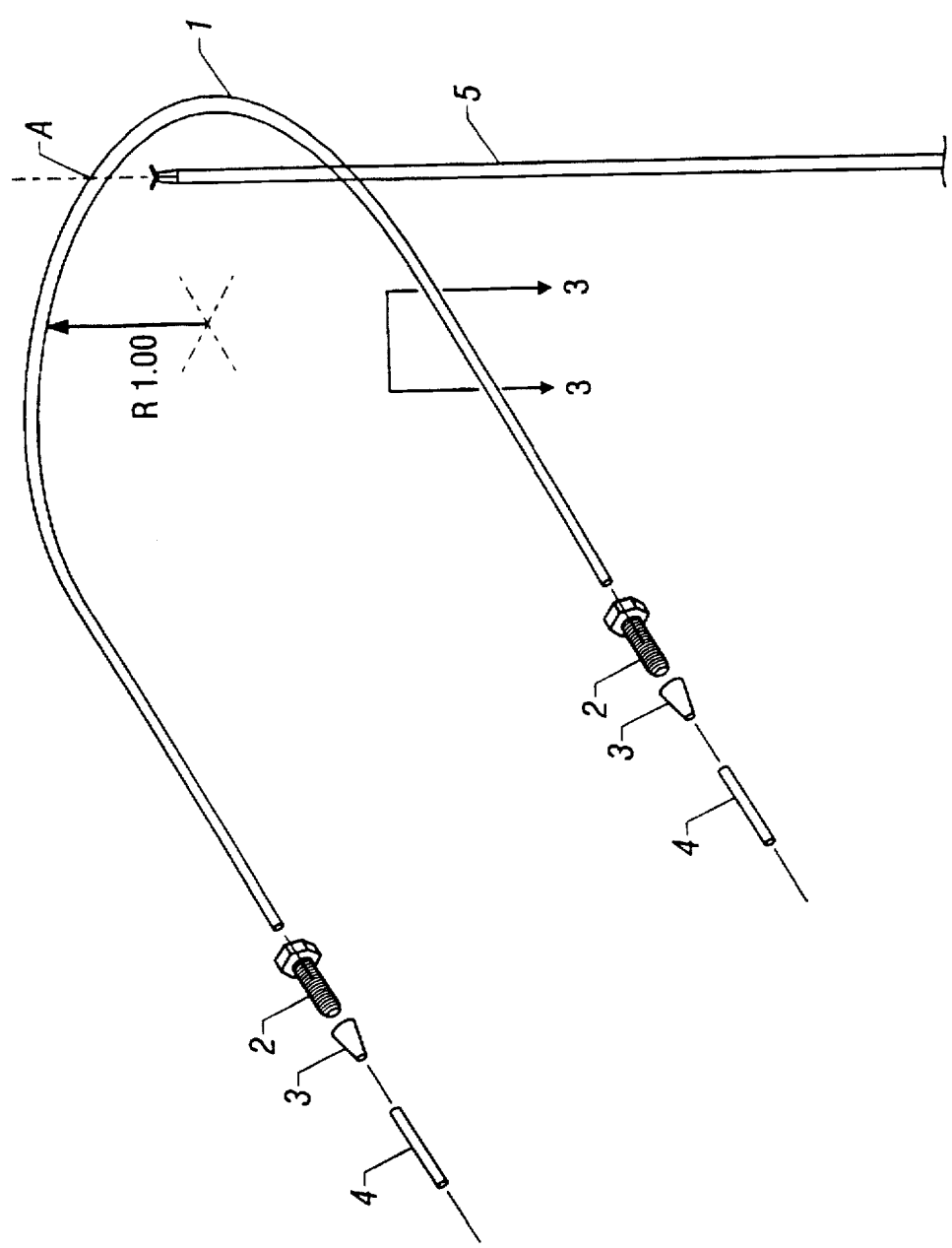
FIG. 3 is an exploded perspective view of an embodiment of the microtrap sample concentrator according to the present invention.
Figure 4:
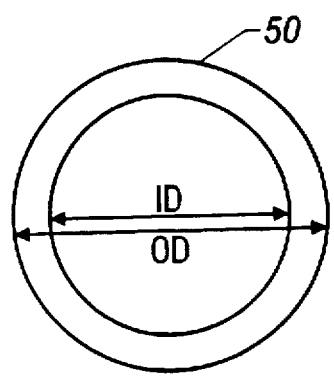
FIG. 4 is a section view taken along section line 3—3 of FIG. 3, showing a transverse section illustrating wall thickness to inner diameter of a preferred embodiment of the microtrap of the claimed invention.

Now referring to FIGS. 3 and 4, a preferred embodiment of the new microtrap sample concentrator 11a is shown.

FIG. 3 is an exploded perspective view of an embodiment of the microtrap sample concentrator according to the present invention. FIG. 3 is drawn here as U-shaped, but the microtrap may also be straight or coiled tubing. The microtrap sample concentrator is a tube ranging in length from approximately 10 cm. (4 inches) to 30.4 cm. (12 inches; 14.6 cm. optimal), having an outside diameter in the range of between 0.050 inches and 0.095 inches (od=0.0625 inches optimal, ≈1/16 inch), having an inside diameter in the range of between 0.045 inches and 0.085 inches (id=0.066 inches optimal). The inventors prefer 25 cm. as optimal length, 0.0625 inches optimal for the od, and 0.066 inches optimal for the id. This tube may be of any alloy but the inventors prefer stainless steel and nickel. This microtrap sample concentrator contains at least one sorbent material which retain volatile organic chemicals (analytes). Different combinations and/or ratios of sorbents may be required depending on the application or method being used and the analytes being studied. At least one sorbent is included in the tube, as many as are desired, e.g., six or seven different sorbents, but the inventors prefer to use about four different sorbents.

In FIG. 3, the #(1) represents the tubing as described above. This tubing may be any alloy but stainless steel or nickel are preferred. Also, #(2) represents a nut (commercially available); #(3) represents ferrule made of stainless steel, 1/16" available from Valco (also commercially available); #(4) represents a sleeve made of stainless steel, inner 18 TW, 18S, #304; #(5) represents a thermocouple assembly type K 30 AWG. The microtrap is packed prior to swaging in inner inserts (B) and the assembly is silver soldered in place (A) prior to packing the trap.

FIG. 4 is a section view taken along section line 3—3 of FIG. 3, showing a transverse section illustrating wall thickness (50) to inner diameter (ID) and outer diameter (OD) of a preferred embodiment of the microtrap of the claimed invention. The ratio of inner diameter to outer diameter is always <1.0 and can range from 0.79 to 0.950 with 0.923 being preferred. The tube size itself can range from an ID/OD of 0.085"/0.095" (ID/OD ratio of 0.89; the largest tube size) to an ID/OD of 0.045"/0.050" (ID/OD ratio of 0.90; the smallest tube size) and 0.060"/0.065" (ratio 0.923) is preferred. Also, the inner diameter of the tube contains at least one sorbent material which retains volatile organic compounds (analytes).

The sorbent materials may be selected from the following group: 2,6-diphenylene oxide polymer, silica gel (15), coconut charcoal (activated charcoal), activated alumina, Carbopack B, Carbopack C, Carbopack F, Carbosieve S-111, Carboxen 1000, Carboxen 1001, Carbowax 20M, Tenax TA, SP-2100/Chromosorb W AW, SP-2250, SP-1200, SP-1000, Porapak Series (N, P, PS, Q, QS, R, S,T,), Porasil, Porasil B, HayeSep Series (A, B, C, D, N, P, Q, R, S), Durapack n-Octane/Porasil C, Molecular Sieve 5A, Molecular Sieve 13X, and Molecular Sieve 4A.

A comparison of the desorption rates and percentage of sample lost due to splitting is presented for the microtrap of the instant invention, and standard purge and trap systems, e.g., OI #4560, Tekmar 3000, is presented below in Table 2. The desorption rate for the microtrap is 1 cc/min with 100% of the sample going to the GC-MS detection system (0% lost via the split interface, "0% split") for all three gas chromatography column sizes (0.25 mm, 0.32 mm, and 0.53 mm). This is in contrast to either the OI #4560 or the Tekmar 3000 purge and trap systems, where the desorption rate is 10 cc/min with only 10% of the sample going to the GC-MS detection system (90% lost via the split interface, "90% split").

TABLE 2

COMPARISON MICROTRAP TO OTHER PURGE & TRAP SAMPLE CONCENTRATORS

| Gas Chromatograph Column ID | .25 mm | .32 mm | .53 mm ("megabore") |
|---|---|---|---|
| Microtrap | Desorb at 1 cc/min 0% Split | Desorb at 1 cc/min 0% Split or Desorb at 2–3 cc/min 0% Split (Conv. Det) or 75% Split (w/MSD) | Desorb at 1 cc/min 0% Split or Desorb at 10 cc/min 0% Split (Conv. Det) or Jet Sep (MSD) |
| OI 4560 | Desorb at 10 cc/min 90% Split | Not Optimal Possible with advanced MS pump System or Desorb at 10 cc/min with 85% Split | Desorb at 10 cc/min 0% Split (Conv. Det) or Jet Sep (MSD) |
| Tekmar 3000 | Desorb at 10 cc/min 90% Split | Not Optimal Possible with advanced MS pump System or Desorb at 10 cc/min with 85% Split | Desorb at 10 cc/min 0% Split (Conv. Det) or Jet Sep (MSD) |

EXAMPLE 1

A New Purge and Trap Sample Concentrator Optimized for Low Desorb Flow Operation The objective of this example was to improve the performance of a purge and trap sample concentrator by optimizing the sample path for operation at lower flow rates during the desorption step. The operation at lower flow rates make the sample concentrator more suitable for use with gas chromatograph capillary columns.

Experimental Design

In order to optimize flow rates during the desorption step, a trap was constructed of 1/16 inch steel tubing and packed with carbon molecular sieve sorbent. The trap was installed in a modified OI Analytical Model #4560 Purge and Trap Sample Concentrator, with all the tubing in the concentrator appropriately sized for narrow bore column flow rates and with all the dead volumes in the system minimized. The trap was heated by direct resistance heating and was heated to 250° C., from ambient temperature, in less than 15 seconds.

This new purge and trap sample concentrator was operated using standard conditions of eleven minute (11') purge, four minute (4') desorb, and ten minute (10') bake times. The trap was near ambient temperature (approximately 23° C.) during purge, heated to 250° C. during desorb, and heated to 260° C. during bake. The purge gas flow was forty milliliters per minute, and the desorb gas flow was 1.5 milliliters per minute for two (2) minutes, then 1.0 milliliter per minute for the remainder of the desorb time.

The interface from the purge and trap sample concentrator to the gas chromatograph column was a low dead volume union. The gas chromatograph/mass spectrometer used for this work was a Hewlett Packard Model 5890 Series II Plus interfaced to a Hewlett Packard Model 5972 Mass Selective Detector. The column used was a J&W DB-VRX 60 m×0.25 mm id with a 1.4 micron phase thickness. The column was held at 35° C. for 6 minutes, ramped to 230 ° C. at a rate of 8° C. per minute, and held at 230° C. for 1 minute. The column flow as 1.5 milliliters per minute for 2 minutes, then was held at 1 milliliter per minute for the rest of the run using electronic pressure control. The mass spectrometer was scanned from 35 to 260 daltons with a scan rate of 1.9 scans per second.

Calibration Tests

The standard solutions used in this study were prepared from concentrated standards purchased from Accustandard, 25 Science Park, New Haven, Conn. 06511. The working solutions were prepared from the stock solutions immediately before use.

These standard solutions were prepared over the range of 5 to 200 ppb to determine the performance of the small bore trap of the claimed invention as compared to conventional traps. A set of solutions for the concentration range of 0.25 to 25 ppb was used to determine statistical detection limits following EPA approved procedures.

Standard solutions were also run using the same sample concentrator and gas chromatograph—mass spectrometer system fitted with a conventional 1/8 inch trap. For these runs, the gas chromatograph and mass spectrometer conditions were the same, with the exception of a 20 milliliter per minute desorb flow rate split 19:1 at a capillary split interface. The purge and trap sample concentrator conditions were the same with the exception of a desorb temperature of 180° C. and a bake temperature of 190° C.

RESULTS

Figure 5:
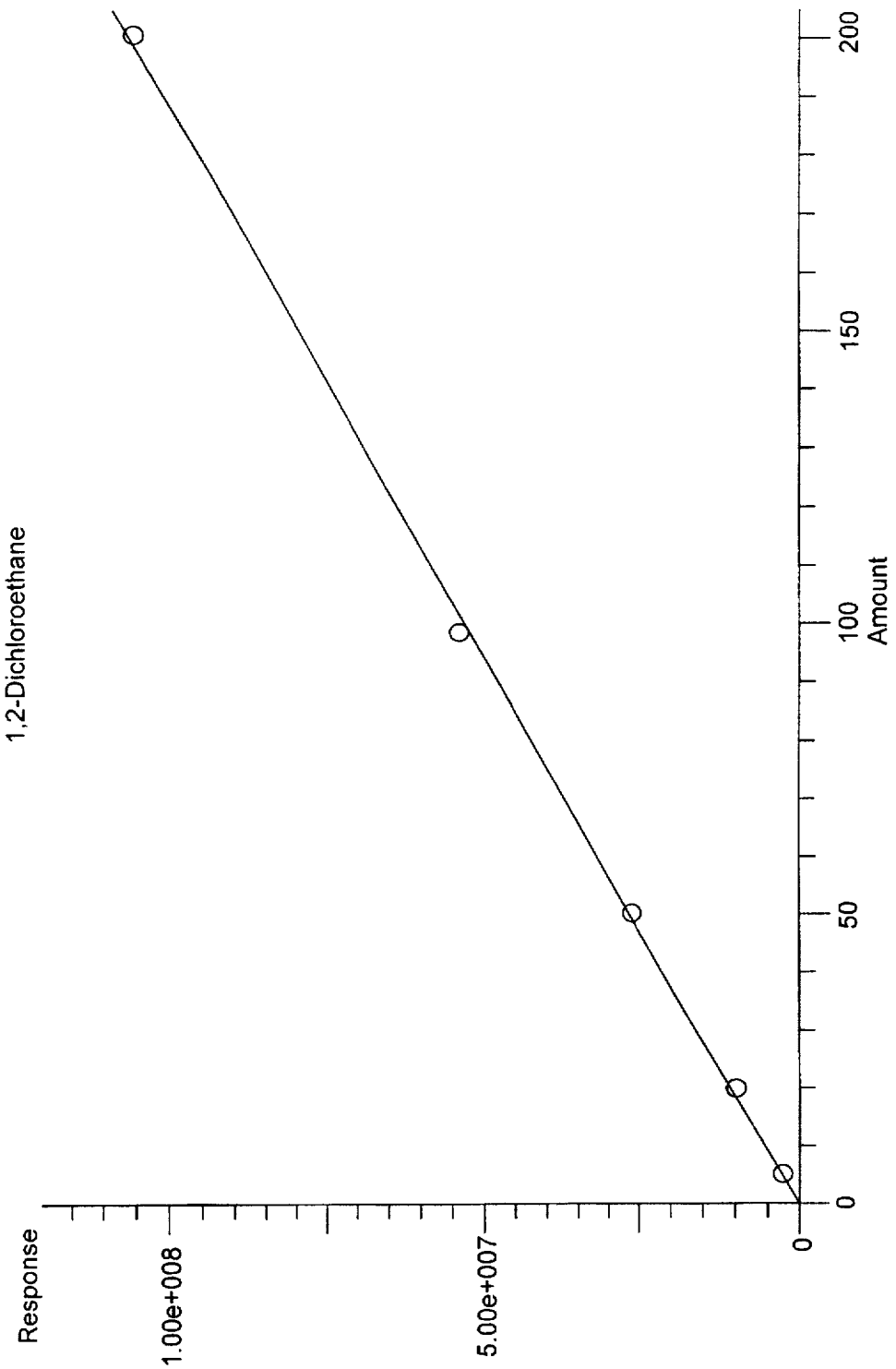
FIG. 5 is a calibration curve for 1,2-dichloroethane over the range of 5 to 200 ppb.
Figure 6:
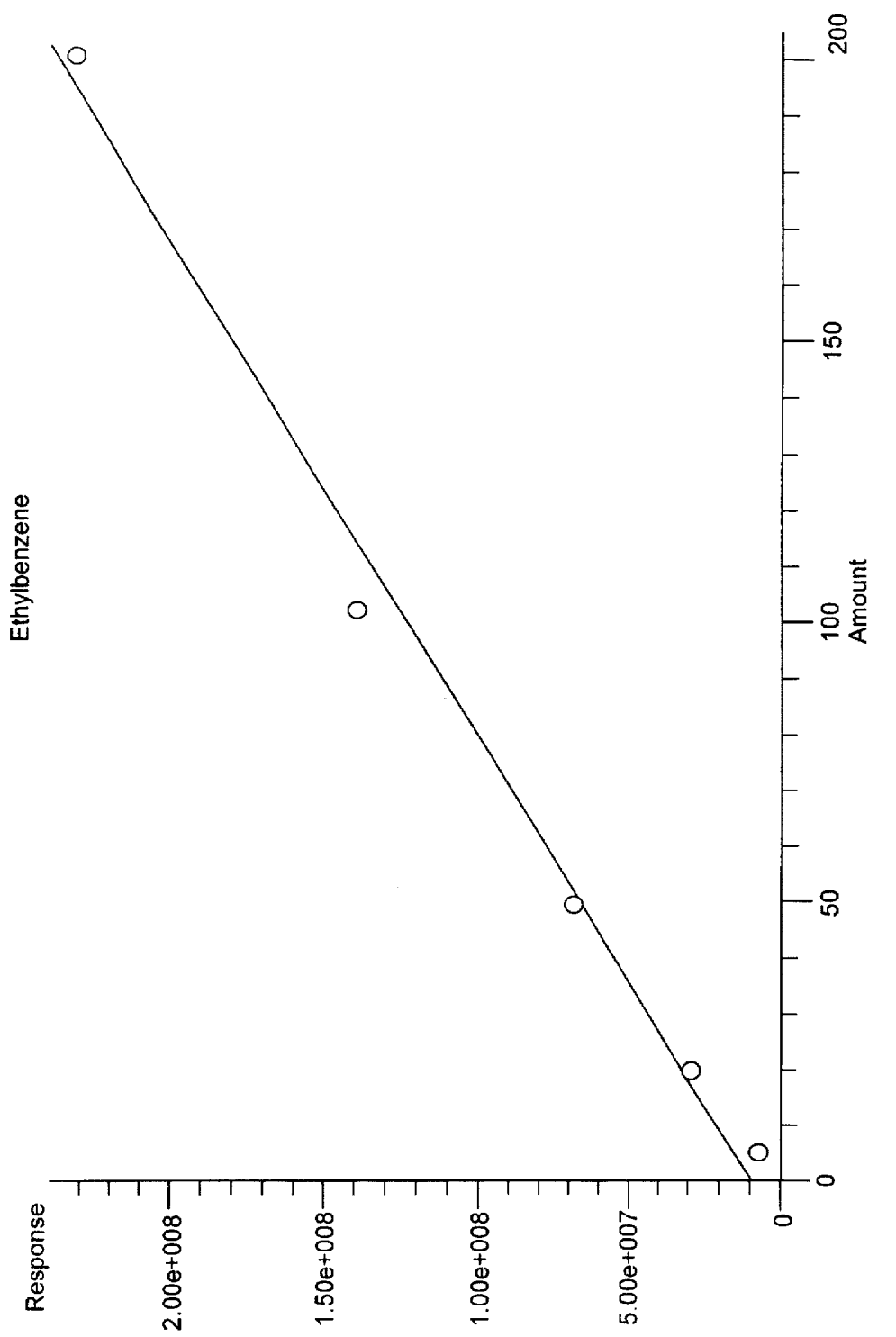
FIG. 6 is a calibration curve for ethylbenzene over the range of 5 to 200 ppb.

The small bore microtrap demonstrated good linearity over the traditional/standard purge and trap range for most of the compounds in the US EPA Method 502.2 list. FIGS. 5 and 6 show calibration curves obtained with the microtrap of the instant invention for typical compounds in the standards used. FIG. 5, the calibration curve for 1,2-dichloroethane, is linear across the standard purge and trap operating range. FIG. 6, the calibration curve for ethylbenzene, shows good linearity but also exceeds the linearity range of the mass spectrometer. The 200 ppb standard overloads the electron multiplier and the response for this compound is lower than expected. This overloading is most likely to occur for compounds with only one or two principal fragments. The majority of compounds will have enough fragments so the response of each fragment will be in the linear range of the electron multiplier.

Figure 7:
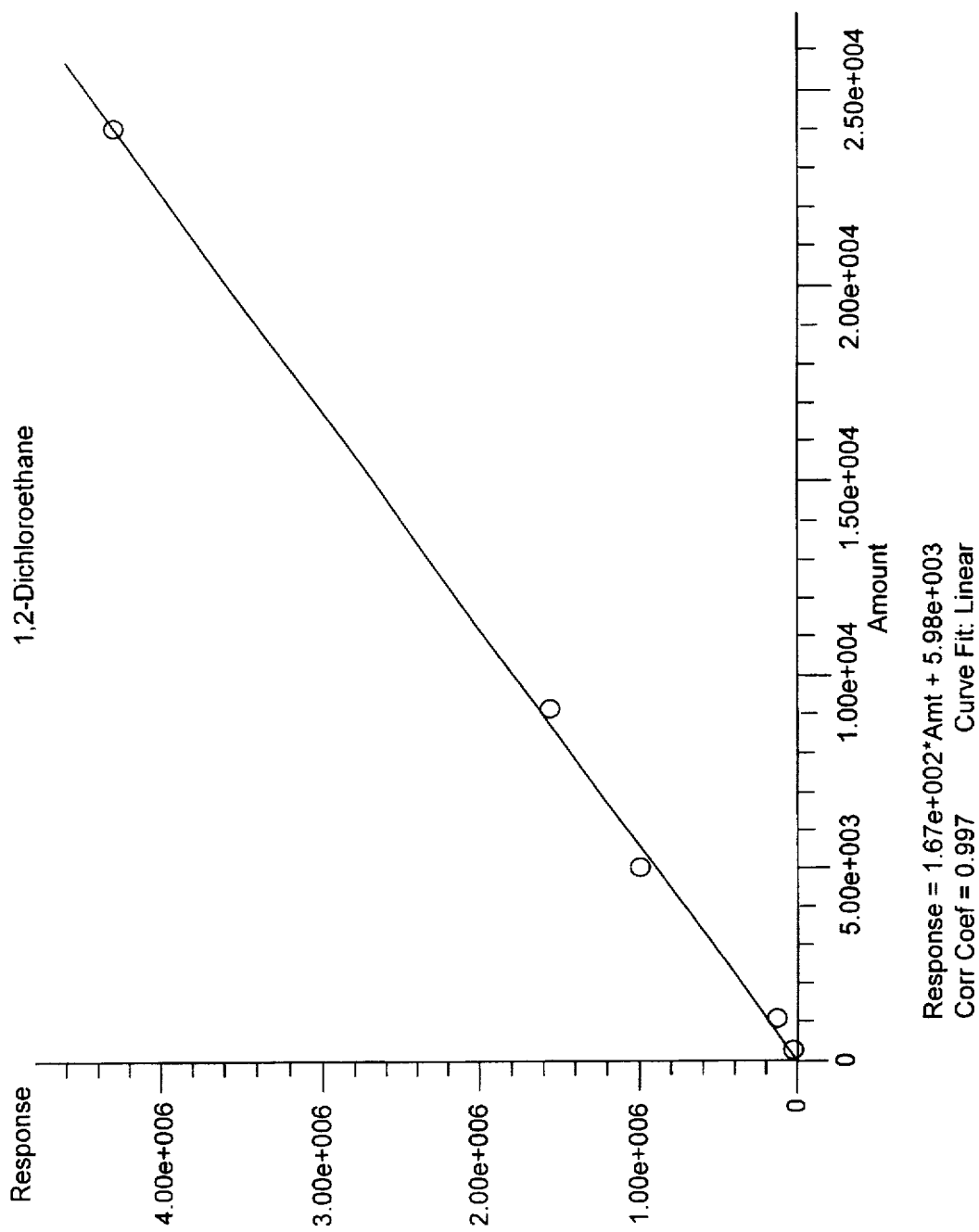
FIG. 7 is a calibration curve for 1,2-dichloroethane over the range of 0.25 to 25 ppb.
Figure 8:
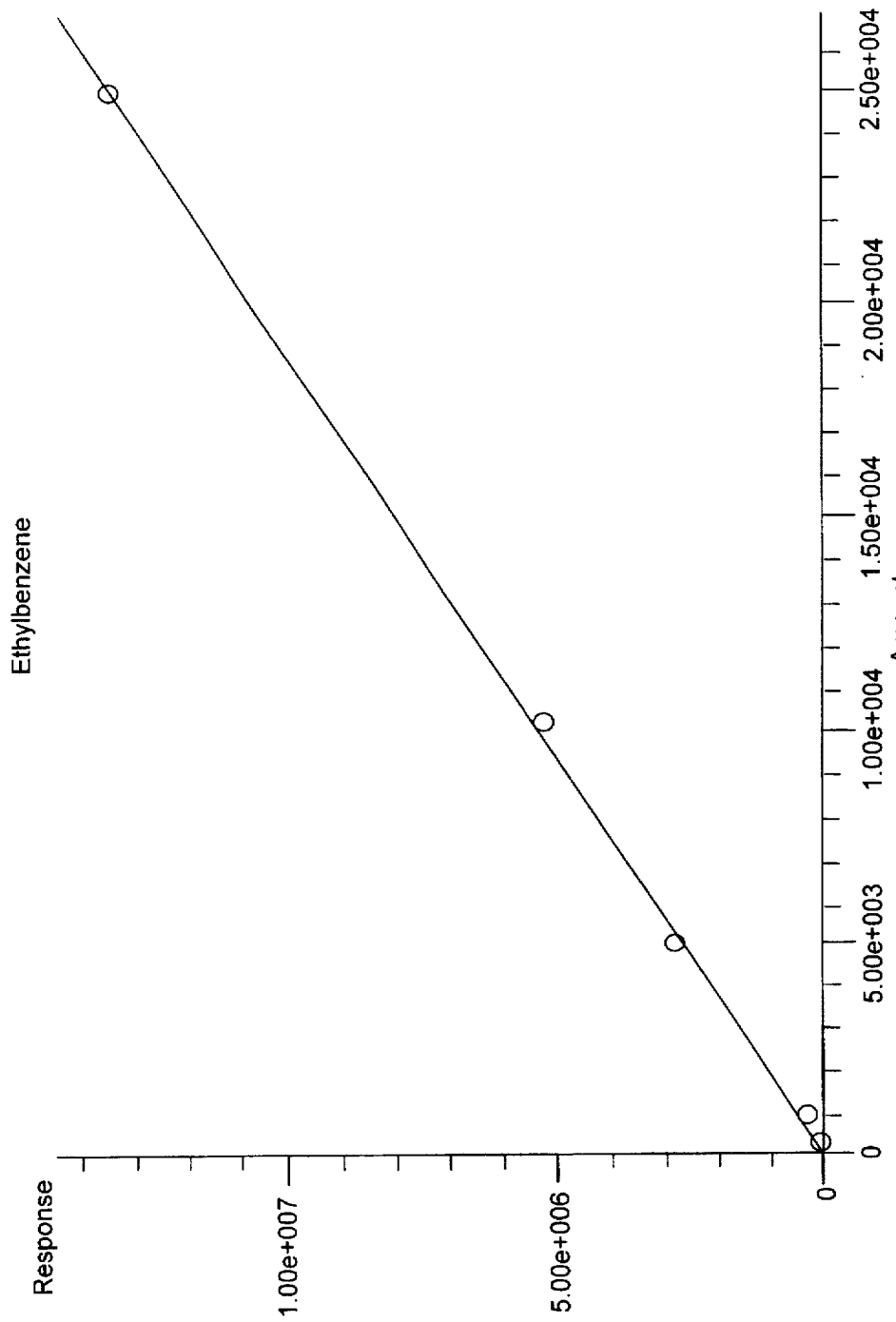
FIG. 8 is a calibration curve for ethylbenzene over the range of 0.25 to 25 ppb.

FIGS. 7 and 8 are calibration curves over the range of 0.25 to 25 ppb for 1,2-dichloroethane and ethylbenzene, respectively, using the microtrap of the instant invention. These curves were generated as part of a study of the detection limits for purge and trap—gas chromatography—mass spectrometry using the splitless interface. The curves show none of the overloading of the electron multiplier seen on the previous curves. The calibration was used to generate detection limits using the statistical method specified by the US EPA.

Figure 9:
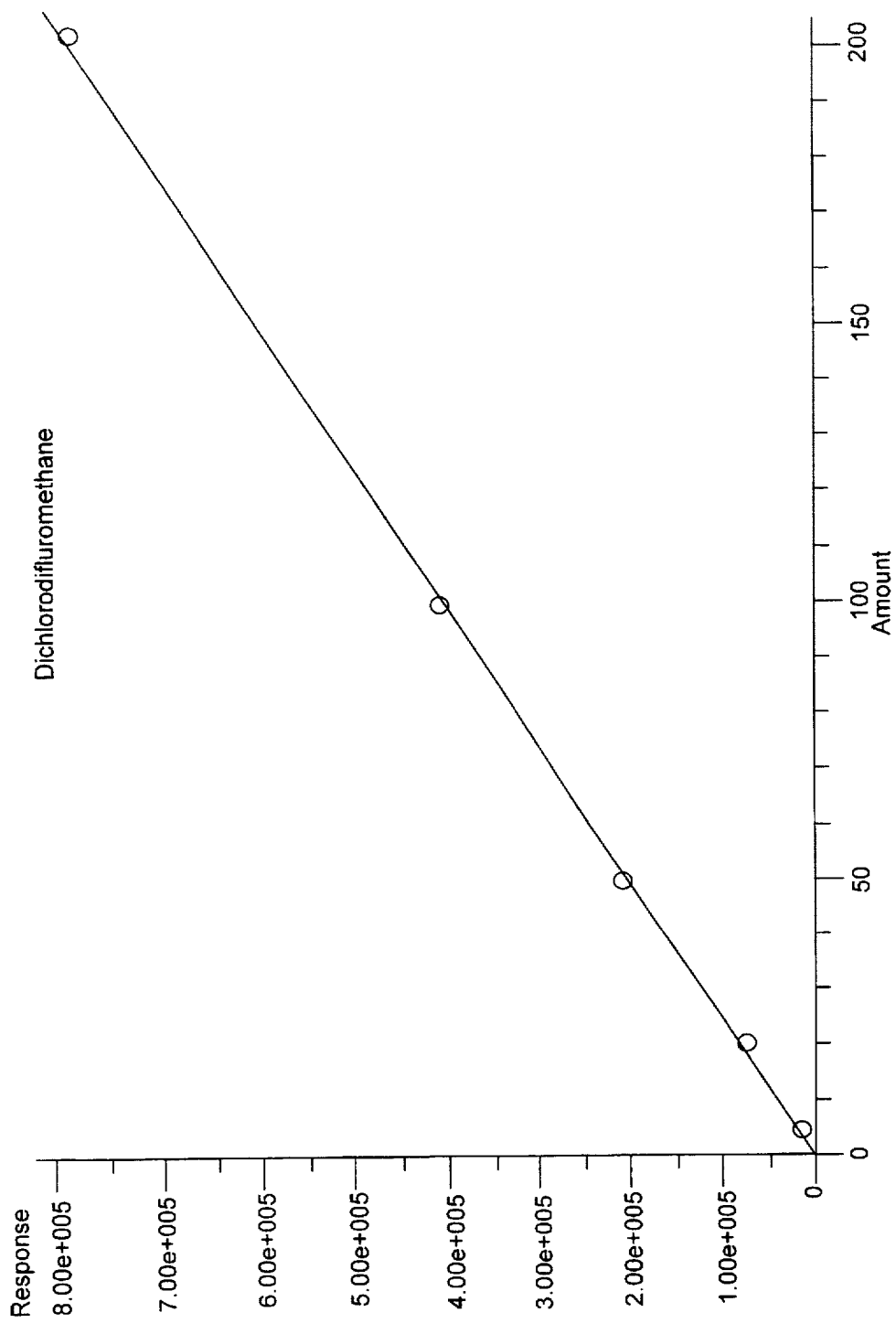
FIG. 9 is a calibration curve for dichlorodifluoromethane over the range of 5 to 200 ppb.
Figure 10:
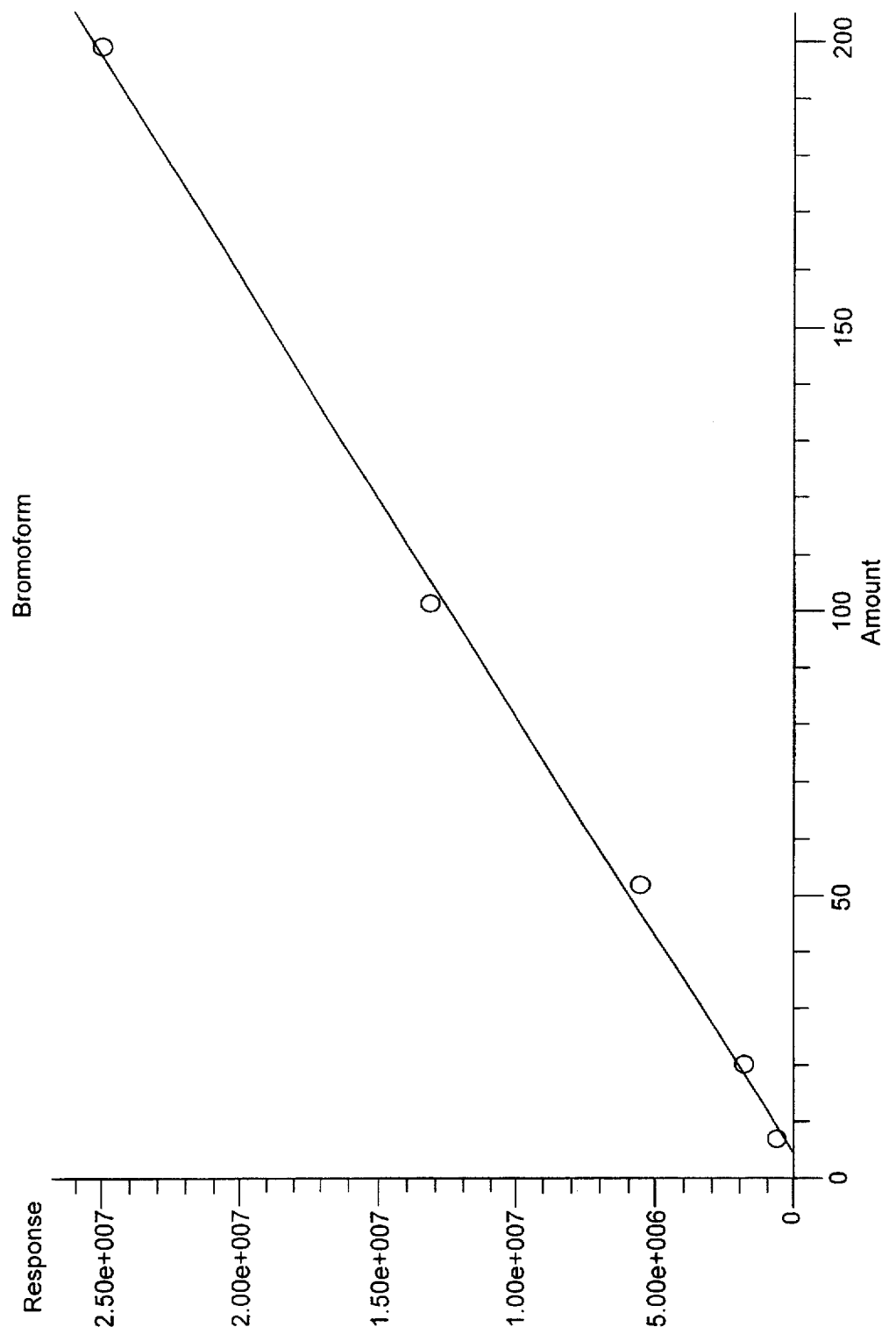
FIG. 10 is a calibration curve for bromoform over the range of 5 to 200 ppb.
Figure 11:
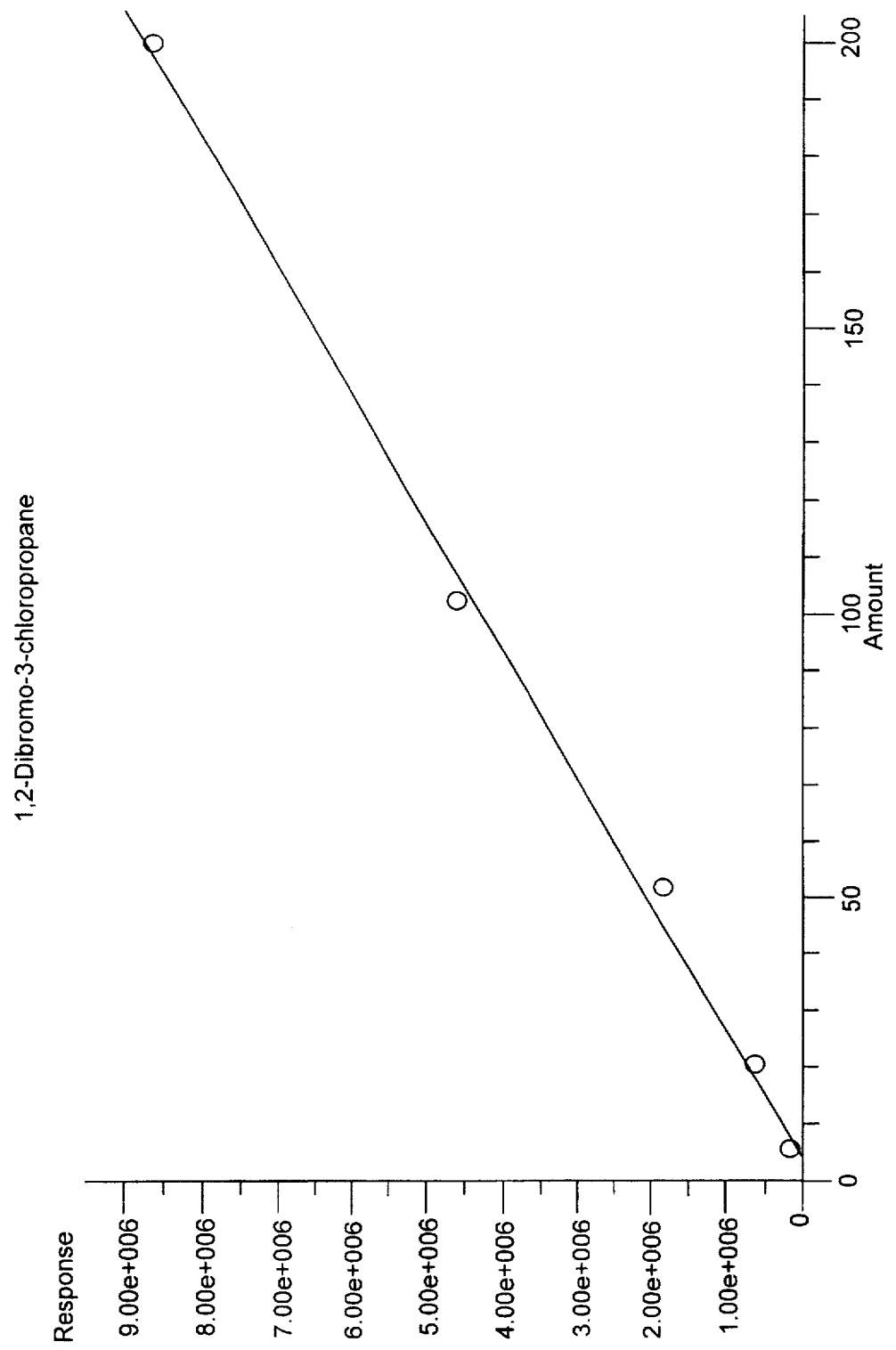
FIG. 11 is a calibration curve for 1,2-dibromo-3-chloropropane over the range of 5 to 200 ppb.

Also FIGS. 9, 10, and 11 are calibration curves for dichlorodifluoromethane, bromoform, and 1,2-dibromo-3-chloropropane, respectively. These calibration studies demonstrated that the microtrap sample concentrator of the claimed invention is very efficient over a broad range of concentrations without losing efficiency via the microtrap itself. Specifically, the saturation/breakthrough of analytes does not occur at normal concentrations encountered in this method, thus smaller sorbent bed volume is adequate for analysis.

Figure 12:
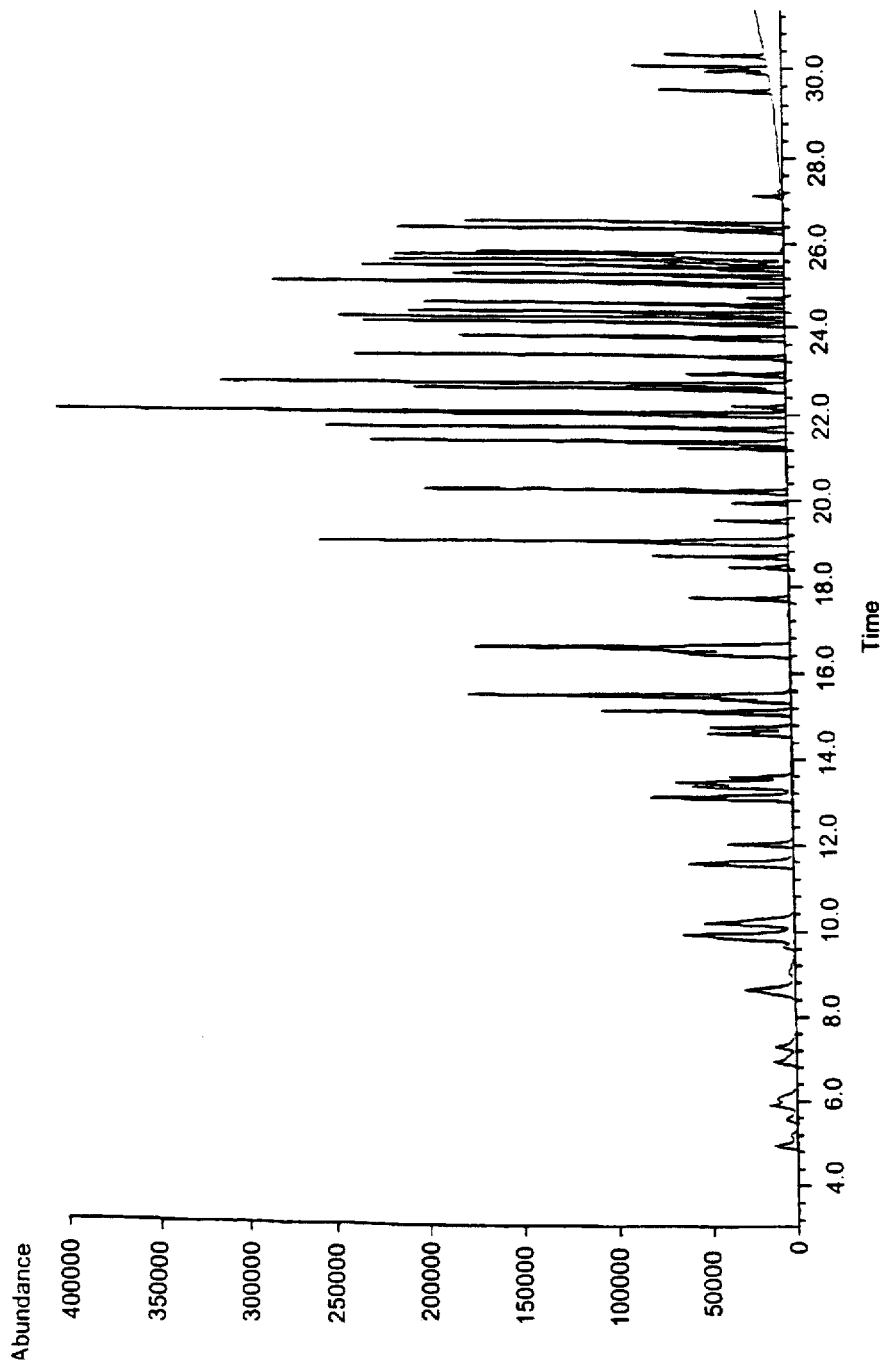
FIG. 12 is a chromatograph showing the sensitivity of the microtrap and the direct connection. This figure should be compared with FIG. 13.
Figure 13:
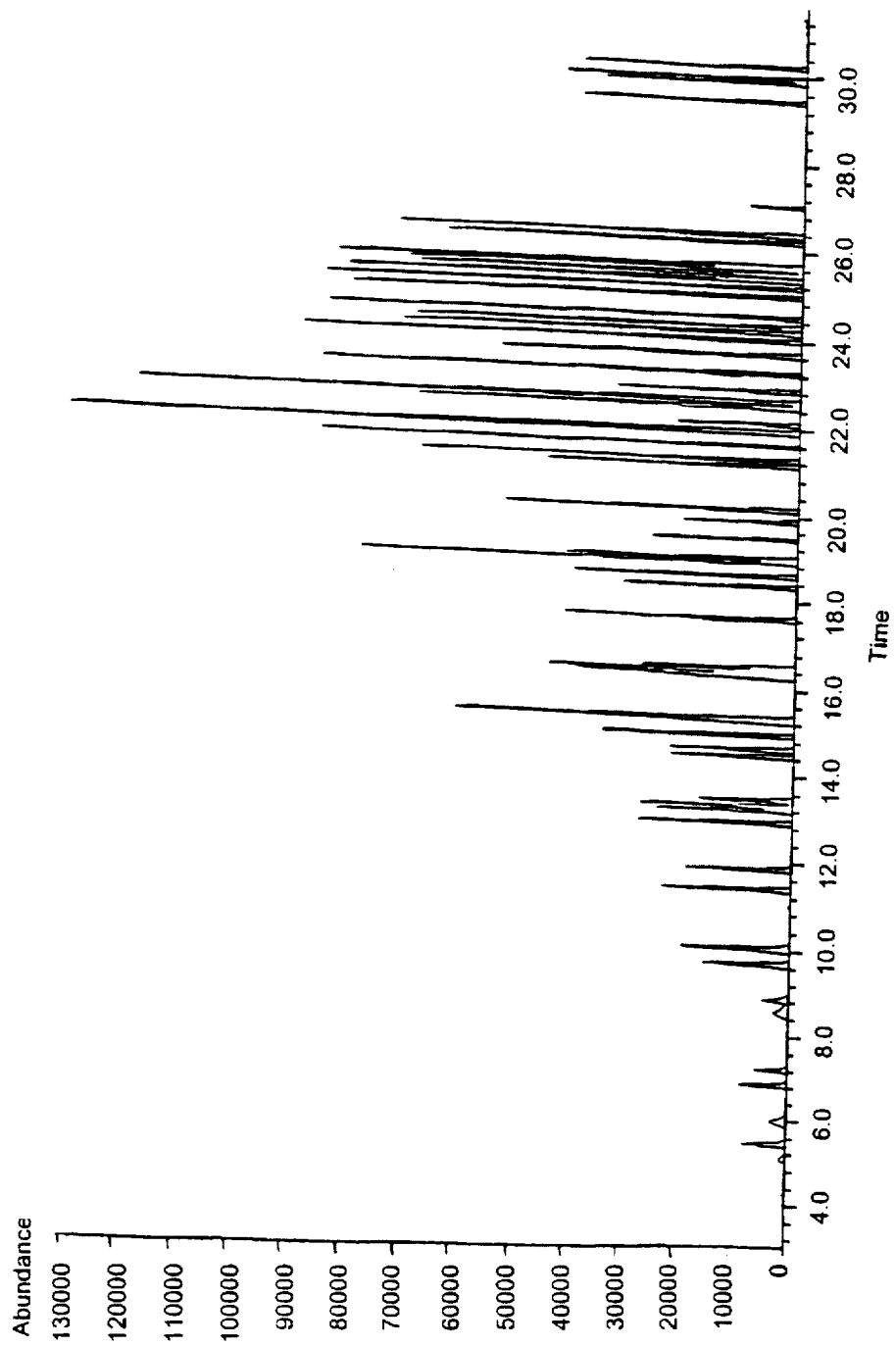
FIG. 13 is a chromatograph showing the sensitivity of a standard trap and a capillary split interface. This figure should be compared with FIG. 12.

FIGS. 12 and 13 illustrate the difference in sensitivity of the microtrap and the direct connection compared to a standard trap and a capillary split interface. The chromatograms were obtained using the same gas chromatograph conditions and the same mass spectrometer conditions. The chromatograms illustrate the gain in sensitivity when a mass spectrometer can be operated with a splitless interface to a purge and trap sample concentrator.

Figure 14:
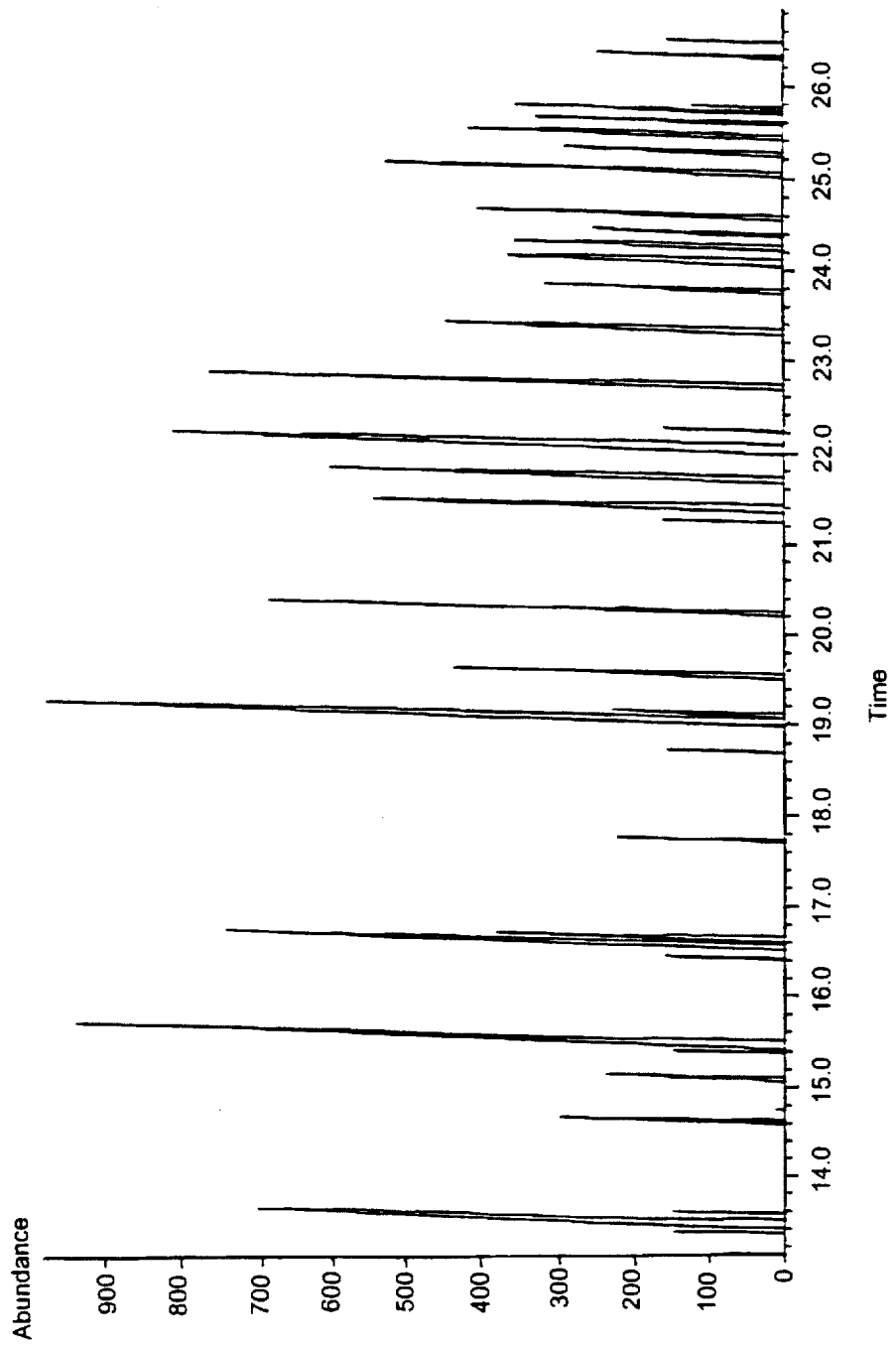
FIG. 14 is a chromatogram of a solution of 50 parts per trillion of the US EPA Method 502.2 analyte list obtained by using the microtrap and the direct connection embodiment according to the claimed invention.

FIG. 14 is a chromatogram of a solution of 50 parts per trillion (0.05 ppb) of the US EPA Method 502.2 analyte list obtained by using the microtrap and the direct connection embodiment according to the claimed invention. The portion of the chromatogram from benzene to the dichlorobenzene is shown. The parent ions for all the compounds are present and can be integrated. With a conventional trap and a split interface similar statistical detection limits may be obtained, but compounds present at concentrations close to the detection limits will not be detected. These data demonstrate the increased sensitivity obtained with the microtrap of the instant invention. These peaks would not have been detected using a standard trap and a split interface, as many of these peaks are below the Minimum Detection Limit (MDL) for the method.

Figure 15:
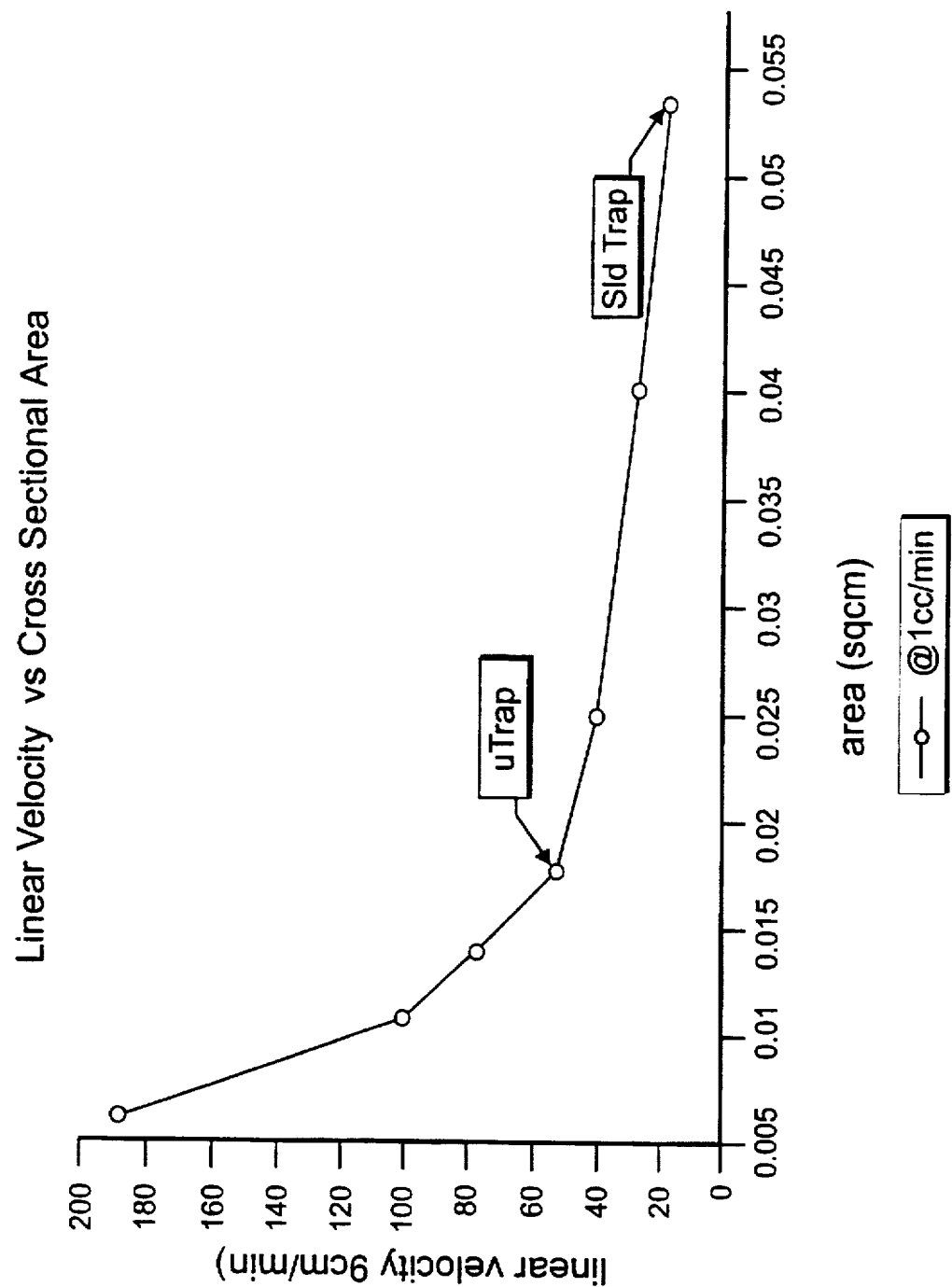
FIG. 15 is a graph showing linear velocity versus cross-sectional area.

FIG. 15 is a graph showing linear velocity versus cross-sectional area. The following can be concluded from this graph. The trap is swept (unloaded) more efficiently at higher linear velocities. The use of the microtrap, with its smaller cross-sectional area and shorter length, results in a significantly higher linear velocity than can be achieved with a conventional standard trap, when operated at the low flow rates dictated by the analytical method. FIG. 15 shows, that at the typical 1 cc/min flow rate, the microtrap shows a three (3) times increase in linear velocity over the standard trap.

Limits of detection (LODs) were determined using U.S. EPA Method 502.2 and the microtrap and were compared to the standard trap (See Table 3 below). Using the microtrap of this invention, the detection limits for 34 compounds ranged from 7 ppt to 78 ppt, with the average detection limit being 31 ppt. Most of the compounds have a calculated detection between 20 ppt and 40 ppt. The mean/average was determined using the microtrap for seven replicates of a 250 ppt solution and is shown in Table 3. The concentration determined for compounds in the middle of the volatility range is generally between 200 and 270 ppt, or 80 to 105% of the expected value. The concentrations determined at the high and low ends of the volatility range tend to be lower, but changes in operating conditions or sorbents will improve accuracy of these determinations. These limits of detection, when compared to the limits of detection obtained with conventional standard purge and trap systems (See Table 3) show a significant improvement in sensitivity (lower detection limits) for the microtrap. The data presented in Table 3 shows that the limits of detection, in ppt, for the microtrap of the instant invention, are approximately four (4) times lower than the limits of detection obtained using standard trap. For example, the limits of detection using the microtrap ranges from 7-78 ppt and the limits of detection for the standard trap ranges from 100-1000 ppt. The best detection limit for the microtrap is 7 ppt and the worst or highest limit of detection is 78 ppt. In contrast, the best limits of detection using the standard trap is 100 ppt which is substantially higher than the worst limit of detection obtained with the microtrap. Thus, with the improved sensitivity of microtrap of the claimed invention, compounds can be detected at much lower levels (7–78 ppt) as compared to the standard trap (100–1000 ppt).

Figure 16:
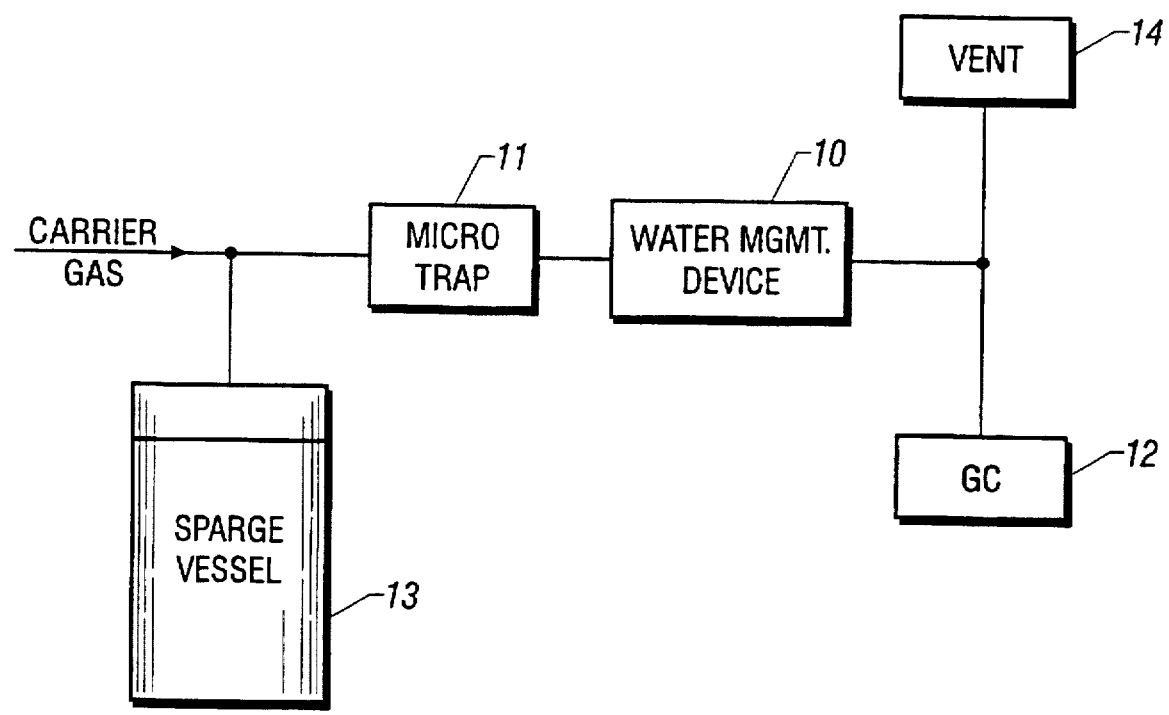
FIG. 16 is a schematic diagram of an alternate sample concentrator/GC system.

FIG. 16 is a schematic diagram of an alternate sample concentrator/GC system. Another advantage to these inventions is that water vapor may be removed from the analyte slug without expensive and complex mechanical or electro-mechanical mechanisms that are subject to failure after repeated cycling.

In an alternative embodiment, the water management device is located between the microtrap and the GC, as shown in FIG. 16, and a length of tubing provides a path between the sparge vessel and the microtrap. In this fore-flush configuration the carrier gas flows through the microtrap in the same direction during the desorb step as the purge gas does during the purge and trap step (or simply "the purge step"). During the purge and trap step, the purge gas is routed through the sparge vessel 13, through the microtrap 11, through the water management device 10 and out vent 14. During the desorb step, the carrier gas is routed through the microtrap, through the water management device and to the GC 12.

The fore-flush configuration is similar to that described above but is different in several important respects. As before, this process is microprocessor controlled with certain parameters that may be selected by the operator.

TABLE 3

LIMITS OF DETECTION COMPARING MICROTRAP AND STANDARD TRAP USING US EPA METHOD 502.2

| Compound | MICROTRAP | | STANDARD TRAP | |
| --- | --- | --- | --- | --- |
| | LOD | Mean | LOD | Mean |
| Dichlorodifluoromethane | 65 | 127 | 300 | 960 |
| Vinyl chloride | 69 | 155 | 300 | 980 |
| Bromomethane | 78 | 237 | | |
| 1,1-Dichloroethene | 47 | 152 | 200 | 1009 |
| Methylene chloride | 32 | 197 | 1000 | 990 |
| trans-1,2-Dichloroethene | 21 | 206 | 200 | 980 |
| 1,1-Dichloroethane | 20 | 219 | | |
| cis-1,2-Dichloroethene | 14 | 215 | | |
| Chloroform | 24 | 249 | 200 | 1003 |
| 1,1,1-Trichloroethane | 36 | 257 | 300 | 1005 |
| Carbon tetrachloride | 49 | 237 | 300 | 880 |
| Benzene | 8 | 230 | 100 | 970 |
| 1,2-Dichloropropane | 25 | 233 | 200 | 1001 |
| Trichloroethene | 19 | 201 | 400 | 900 |
| cis-1,3-dichloropropene | 21 | 227 | | |
| trans-1,3-Dichloropropene | 30 | 227 | | |
| 1,1,2-Trichloroethane | 37 | 189 | | |
| Toluene | 16 | 199 | 100 | 1005 |
| 1,3-Dichloropropane | 15 | 210 | 100 | 1000 |
| Dibromochloromethane | 32 | 257 | 400 | 920 |
| 1,2-Dibromoethane | 37 | 217 | 400 | 930 |
| Tetrachloromethane | 26 | 197 | | |
| Chlorobenzene | 14 | 214 | 100 | 1002 |
| Ethylbenzene | 32 | 187 | | |

TABLE 3-continued

LIMITS OF DETECTION COMPARING MICROTRAP AND
STANDARD TRAP USING US EPA METHOD 502.2

| Compound | MICROTRAP | | STANDARD TRAP | |
|---|---|---|---|---|
| | LOD | Mean | LOD | Mean |
| m-&p-Xylene | 48 | 337 | | |
| Bromoform | 28 | 203 | 700 | 2400 |
| 1,1,2,2-Tetrachloroethane | 22 | 250 | 400 | 1110 |
| 1,2,3-Trichloropropane | 7 | 166 | | |
| Isopropylbenzene | 27 | 187 | | |
| 2-Chlorotoluene | 24 | 185 | | |
| 1,3,5-Trimethylbenzene | 40 | 160 | | |
| 1,4-Dichlorobenzene | 27 | 161 | 2000 | 5600 |
| Isopropyltoluene | 38 | 170 | | |
| Hexachlorobutadiene | 14 | 111 | | |

Mean: ppt; The average concentration (mean) determined for seven replicates of a 250 ppt solution.
LOD: Limits of Detection = Method of Detection Limit in parts per trillion (ppt)

SUMMARY

The small bore microtrap sample concentrator of this invention for purge and trap offers significant benefits compared to the conventional standard trap. The trapping capacity of the smaller microtrap is sufficient for the concentration ranges specified in the method. The smaller size and lower mass of the microtrap increases the heating rate of the trap, improves the chromatography, and increases the sensitivity. The ability to efficiently desorb at a lower flow rate (one to three cc/min) allows a purge and trap sample concentrator to be directly interfaced to a gas chromatograph—mass spectrometer detection system, thereby requiring no splitting of the sample nor any cryogenic focusing. The microtrap of this invention can be used with a gas chromatograph equipped with conventional detectors to interface to narrower bore columns, thereby decreasing run times without sacrificing resolution.

Although variations in the embodiments of the present invention may not each realize all the advantages of the invention, certain features may become more important than others in various application of the apparatus and device. The invention, accordingly, should be understood to be limited only by the scope of the appended claims.

What is claimed is:

1. A method of delivering greater than 30% of concentrated analytes to an analytical instrument comprising:
   a) purging or drawing an analyte stream from a sparge vessel containing a sample;
   b) passing the purged analytes through a first passage connecting the sparge vessel to a microtrap where the analytes associate with one or more sorbent material contained within the microtrap; and
   c) desorbing the analyte stream from the microtrap at a desorption flow rate of one to three cc/min and directly passing greater than 30% of the desorbed analyte stream through a second passage from the microtrap to an analytical instrument, without first splitting or cryogenically focusing the analyte stream,
   wherein the temperature of the second passage is not lower than ambient room temperature;
   and wherein the second passage is heated by a heating means to a temperature sufficient to vaporize water in the passage and to expel the vaporized water out of a vent.

2. The method of claim 1 wherein the second passage is configured to impart an angular velocity on the analytes flowing from the microtrap to the analytical instrument.

3. The method of claim 1 wherein the microtrap comprises:
   a) a tube containing said one or more sorbent material wherein the analytes associate with said one or more sorbent material contained within the microtrap thereby trapping or retaining the analytes.

4. The method of claim 3 wherein the tube is of hypodermic or instrument grade and wherein the shape of the tube is selected from the group consisting of straight, U-shaped, and coiled.

5. The method of claim 3 wherein the tube is selected from the group consisting of stainless steel and nickel.

6. The method of claim 5 wherein the stainless steel is selected from the group consisting of stainless steel Type 304, stainless steel Type 303, stainless steel Type 316, stainless steel Type 416, stainless steel Type 446, and stainless steel Type 326.

7. The method of claim 5 wherein the nickel is nickel 200 alloy.

8. The method of claim 3 wherein the tube is approximately 10 cm. (4 inches) to 30 cm. (12 inches) long, having an outside diameter in the range of between 0.050 inches and 0.095 inches, having an inside diameter in the range of between 0.045 inches and 0.085 inches.

9. The method of claim 3 wherein said one or more sorbent material is selected from the group consisting of 2,6-diphenylene oxide polymer, silica gel, coconut charcoal (activated charcoal), activated alumina, Carbopack B, Carbopack C, Carbopack F, Carbosieve S-111, Carboxen 1000, Carboxen 1001, Carbowax 20M, Tenax TA, SP-2100/Chromosorb W AW, SP-2250, SP-1200, SP-1000, Porapak Series (N, P, PS, Q, QS, R, S, T), Porasil, Porasil B, HayeSep Series (A, B, C, D, N, P, Q, R, S), Durapak n-Octane/Porasil C, Molecular Sieve 5A, Molecular Sieve 13X, and Molecular Sieve 4A.

10. The method of claim 3 wherein the tube has an inner diameter/outer diameter ratio ranging from about 0.085"/0.095" to about 0.045"/0.050".

11. The method of claim 10 wherein the inner diameter/outer diameter ratio of the tube is about 0.060"/0.065".

12. The method of claim 3 wherein the inner diameter of the tube is of such a size that the trap volume per minute at a one cc/min desorption flow rate is between about 2.5 and about 4.5, the linear velocity at a desorption flow rate of one cc/min is between about 0.700 cm/second and about 1.0 cm/second and the heating rate is between about 1200° C./min and about 1800° C./min.

13. The method of claim 12 wherein the inner diameter/outer diameter ratio of the tube ranges from about 0.085"/0.095" to about 0.045"/0.050".

14. The method of claim 13 wherein the inner diameter/outer diameter ratio of the tube is about 0.060"/0.065".

15. The method of claim 1 wherein the analytical instrument is a gas chromatograph comprising a gas chromatograph column.

16. The method of claim 15 wherein the gas chromatograph column has an inner diameter of less than 0.45 mm.

17. The method of claim 1 wherein the analytes are purged or drawn from a sample derived from the group consisting of water, soil, food, beverage, pharmaceutical products, biological samples, forensic samples, air samples, gaseous samples, polymers, and sediment matrices.

18. The method of claim 1 wherein greater than 90% of all trapped analytes are directly delivered to the analytical instrument at a desorption flow rate of one to three cc/min, without splitting or cryogenic focusing the trapped analytes.

19. The method of claim 1 wherein 100% of all trapped analytes are directly delivered to the analytical instrument at a desorption flow rate of one to three cc/min, without splitting or cryogenic focusing the trapped analytes.

20. A microtrap sample concentrator useful for concentrating a sample of purged gas containing analytes for delivery to an analytical instrument, comprising:
   a) a tube containing one or more sorbent material which retains or traps analytes;
      wherein greater than 30% of all trapped analytes are directly delivered to an analytical instrument at a desorption flow rate of one to three cc/min, without splitting or cryogenic focusing the trapped analytes;
      wherein delivery of the trapped analytes to the analytical instrument is achieved by passing the trapped analytes through a passage being selectively connectable between the microtrap and the analytical instrument, the passage connected to a vent;
      wherein the temperature of the passage is not lower than ambient room temperature;
   and wherein the passage is heated by a heating means to a temperature sufficient to vaporize water in the passage and to expel the vaporized water out of the vent.

21. The microtrap sample concentrator of claim 20 wherein the passage is configured to impart an angular velocity on the analytes flowing from the microtrap to the analytical instrument.

22. The microtrap sample concentrator of claim 20 wherein the tube is of hypodermic or instrument grade and wherein the shape of the tube is selected from the group consisting of straight, U-shaped, and coiled.

23. The microtrap sample concentrator of claim 20 wherein the tube is selected from the group consisting of stainless steel and nickel.

24. The microtrap sample concentrator of claim 23 wherein the stainless steel is selected from the group consisting of stainless steel Type 304, stainless steel Type 303, stainless steel Type 316, stainless steel Type 416, stainless steel Type 446, and stainless steel Type 326.

25. The microtrap sample concentrator of claim 23 wherein the nickel is nickel 200 alloy.

26. The microtrap sample concentrator of claim 20 wherein the tube is approximately 10 cm. (4 inches) to 30 cm. (12 inches) long, having an outside diameter in the range of between 0.050 inches and 0.095 inches, having an inside diameter in the range of between 0.045 inches and 0.085 inches.

27. The microtrap concentrator of claim 20 wherein said one or more sorbent material is selected from the group consisting of 2,6-diphenylene oxide polymer, silica gel, coconut charcoal (activated charcoal), activated alumina, Carbopack B, Carbopack C, Carbopack F, Carbosieve S-111, Carboxen 1000, Carboxen 1001, Carbowax 20M, Tenax TA, SP-2100/Chromosorb W AW, SP-2250, SP-1200, SP-1000, Porapak Series (N, P, PS, Q, QS, R, S, T), Porasil, Porasil B, HayeSep Series (A, B, C, D, N, P, Q, R, S), Durapak n-Octane/Porasil C, Molecular Sieve 5A, Molecular Sieve 13X, and Molecular Sieve 4A.

28. The microtrap sample concentrator of claim 20 wherein the analytical instrument is a gas chromatograph comprising a gas chromatograph column.

29. The microtrap sample concentrator of claim 28 wherein the gas chromatograph column has an inner diameter of less than 0.45 mm.

30. The microtrap sample concentrator of claim 20 wherein the tube has an inner diameter/outer diameter ratio ranging from about 0.085"/0.095" to about 0.045"/0.050".

31. The microtrap sample concentrator of claim 30 wherein the inner diameter/outer diameter ratio of the tube is about 0.060"/0.065".

32. The microtrap sample concentrator of claim 20 wherein the inner diameter of the tube is of such a size that the trap volume per minute at a one cc/min desorption flow rate is between about 2.5 and about 4.5, the linear velocity at a desorption flow rate of one cc/min is between about 0.700 cm/second and about 1.0 cm/second and the heating rate is between about 1200° C./min and about 1800° C./min.

33. The microtrap sample concentrator of claim 32 wherein the inner diameter/outer diameter ratio of the tube ranges from about 0.085"/0.095" to about 0.045"/0.050".

34. The microtrap sample concentrator of claim 33 wherein the inner diameter/outer diameter ratio of the tube is about 0.060"/0.050".

35. The microtrap sample concentrator of claim 20 wherein the analytes are purged or drawn from a sample derived from the group consisting of water, soil, food, beverage, pharmaceutical products, biological samples, forensic samples, air samples, gaseous samples, polymers, and sediment matrices.

36. The microtrap sample concentrator of claim 20 wherein greater than 90% of all trapped analytes are directly delivered to the analytical instrument at a desorption flow rate of one to three cc/min, without splitting or cryogenic focusing the trapped analytes.

37. The microtrap sample concentrator of claim 20 wherein 100% of all trapped analytes are directly delivered to the analytical instrument at a desorption flow rate of one to three cc/min, without splitting or cryogenic focusing the trapped analytes.

38. An apparatus for removal of water from analytes being purged from a sparge vessel to a microtrap and desorbed from the microtrap to an analytical instrument, comprising:
   (a) a purge means or a draw means for purging or drawing the analytes from a sparge vessel and passing the purged analytes through a first passage connecting the sparge vessel to a microtrap;
   (b) desorbing means for desorbing the analytes from the microtrap and passing the desorbed analytes through a second passage from the microtrap to an analytical instrument, the second passage being configured to impart an angular velocity on the analytes flowing from the microtrap to the analytical instrument, and wherein the temperature of the second passage is not lower than ambient room temperature; and
   (c) heating means for heating the second passage to a temperature sufficient to expel water vapor from the passage through a vent.

39. The apparatus of claim 38 wherein the second passage imparts angular velocity on the analyte stream by causing the analyte stream to flow in a helical path through the second passage during use of the desorbing means.

40. The apparatus of claim 38 wherein the second passage imparts angular velocity on the analyte stream by causing the analyte stream to flow in a cylindrical path through the second passage during use of the desorbing means.

41. The apparatus of claim 38 wherein the second passage is thermally isolated from the microtrap.

42. The apparatus of claim 38 further comprising a fan for cooling the second passage.

43. The apparatus of claim 38 wherein the analytes flow through the second passage in opposite directions during purging and desorption.

44. The apparatus of claim 38 wherein the second passage retains enough heat during purging to substantially prevent condensation of water in the second passage.

45. The apparatus of claim 38 wherein a heating cartridge and thermocouple comprise the heating means for heating the second passage.

46. The apparatus of claim 38 wherein the second passage imparts angular velocity on the analyte stream by spiraling the analyte stream during use of the desorbing means.

47. The apparatus of claim 38 wherein the microtrap comprises:

a) said desorbing means for desorbing the analytes from the microtrap comprising a tube containing one or more sorbent material wherein the analytes associate with at least one of said sorbent material contained within the microtrap thereby trapping or retaining the analytes;

and wherein greater than 30% of all trapped analytes are directly delivered through said second passage from the microtrap to an analytical instrument at a desorption flow rate of one to three cc/min, without splitting or cryogenic focusing the trapped analytes, and wherein the said second passage is configured to impart an angular velocity on the analytes flowing from the microtrap to the analytical instrument.

48. The apparatus claim 47 wherein the tube is of hypodermic or instrument grade and wherein the shape of the tube is selected from the group consisting of straight, U-shaped, and coiled.

49. The apparatus of claim 47 wherein the tube is selected from the group consisting of stainless steel and nickel.

50. The apparatus of claim 49 wherein the stainless steel is selected from the group consisting of stainless steel Type 304, stainless steel Type 303, stainless steel Type 316, stainless steel Type 416, stainless steel Type 446, and stainless steel Type 326.

51. The apparatus of claim 49 wherein the nickel is nickel 200 alloy.

52. The apparatus of claim 47 wherein the tube is approximately 10 cm. (4 inches) to 30 cm. (12 inches) long, having an outside diameter in the range of between 0.050 inches and 0.095 inches, having an inside diameter in the range of between 0.045 inches and 0.085 inches.

53. The apparatus of claim 47 wherein said one or more sorbent material is selected from the group consisting of 2,6-diphenylene oxide polymer, silica gel, coconut charcoal (activated charcoal), activated alumina, Carbopack B, Carbopack C, Carbopack F, Carbosieve S-111, Carboxen, 1000, Carboxen 1001, Carbowax 20M, Tenax TA, SP-2100/ Chromosorb w AW, SP-2250, SP-1200, SP-1000, Porapak Series (N, P, PS, Q, QS, R, S, T), Porasil, Porasil B, HayeSep Series (A, B, C, D, N, P, Q, R, S), Durapak n-Octane/Porasil C, Molecular Sieve 5A, Molecular Sieve 13X, and Molecular Sieve 4A.

54. The apparatus of claim 47 wherein the tube has an inner diameter/outer diameter ratio ranging from about 0.085"/0.095" to about 0.045"/0.050".

55. The apparatus of claim 54 wherein the inner diameter/outer diameter ratio of the tube is about 0.060"/0.065".

56. The apparatus of claim 47 wherein greater than 90% of all trapped analytes are directly delivered to the analytical instrument at a desorption flow rate of one to three cc/min, without splitting or cryogenic focusing the trapped analytes.

57. The apparatus of claim 47 wherein 100% of all trapped analytes are directly delivered to the analytical instrument at a desorption flow rate of one to three cc/min, without splitting or cryogenic focusing the trapped analytes.

58. The apparatus of claim 38 wherein the inner diameters of the first passage and second passage are of such a size that the trap volume per minute at a one cc/min desorption flow rate is between about 2.5 and about 4.5, the linear velocity at a desorption flow rate of one cc/min is between about 0.700 cm/second and about 1.0 cm/second and the heating rate is between about 1200 degrees(C.)/min and 1800 degrees (C.)/min.

59. The apparatus claim 58 wherein the tube has an inner diameter/outer diameter ratio ranging from about 0.085"/0.095" to about 0.045"/0.050".

60. The apparatus of claim 59 wherein the inner diameter/outer diameter ratio of the tube is about 0.060"/0.050".

61. The apparatus of claim 38 wherein the analytical instrument is a gas chromatograph comprising a gas chromatograph column.

62. The apparatus of claim 61 wherein the gas chromatograph column has an inner diameter of less than 0.45 mm.

63. A microtrap sample concentrator useful for concentrating a sample of purged gas containing analytes for delivery to an analytical instrument, comprising:

a) a tube containing one or more sorbent material which retains or traps analytes;

wherein greater than 30% of all trapped analytes are directly delivered to an analytical instrument at a desorption flow rate of one to three cc/min, without splitting or cryogenic focusing the trapped analytes.

64. The microtrap sample concentrator of claim 63 wherein the tube is selected from the group consisting of stainless steel and nickel.

65. The microtrap sample concentrator of claim 63 wherein the tube is approximately 10 cm. (4 inches) to 30 cm. (12 inches) long, having an outside diameter in the range of between 0.050 inches and 0.095 inches, having an inside diameter in the range of between 0.045 inches and 0.085 inches.

\* \* \* \* \*